United States Patent
Bundle et al.

(10) Patent No.: US 7,553,819 B2
(45) Date of Patent: Jun. 30, 2009

(54) MULTIVALENT INHIBITORS OF SERUM AMYLOID P COMPONENT

(75) Inventors: David Bundle, Edmonton (CA); Pavel Kitov, Edmonton (CA); Kenneth Kai-Sing Ng, Calgary (CA); Jason Gay Shuen Ho, Calgary (CA)

(73) Assignee: Theracarb Inc., Calgary, Alberta (CA)

( * ) Notice: Subject to any disclaimer, the term of this patent is extended or adjusted under 35 U.S.C. 154(b) by 167 days.

(21) Appl. No.: 10/556,333

(22) PCT Filed: May 12, 2004

(86) PCT No.: PCT/CA2004/000712

§ 371 (c)(1),
(2), (4) Date: Jul. 31, 2006

(87) PCT Pub. No.: WO2004/099173

PCT Pub. Date: Nov. 18, 2004

(65) Prior Publication Data

US 2007/0042936 A1      Feb. 22, 2007

Related U.S. Application Data

(60) Provisional application No. 60/469,633, filed on May 12, 2003.

(51) Int. Cl.
*A01N 43/04* (2006.01)
*A61K 31/70* (2006.01)

(52) U.S. Cl. .............. 514/25; 514/2; 514/23; 514/24

(58) Field of Classification Search .......... None
See application file for complete search history.

(56) References Cited

U.S. PATENT DOCUMENTS

| 3,862,959 | A | 1/1975 | Kirby et al. |
| 5,962,423 | A | 10/1999 | Bundle et al. |
| 6,103,910 | A | 8/2000 | Hertel et al. |
| 6,126,918 | A | 10/2000 | Pepys et al. |
| 6,262,089 | B1 | 7/2001 | Hertel et al. |
| 6,310,043 | B1 | 10/2001 | Bundle et al. |

FOREIGN PATENT DOCUMENTS

| EP | 0915088 | 5/1999 |
| EP | 1295875 | 3/2003 |
| WO | WO 03/020269 A1 | 3/2003 |

OTHER PUBLICATIONS

Tennent et al. "Serum amyloid P component prevents proteolysis of the amyloid fibrils of Alzheimer disease and systemic amyloidosis" *Proc. Natl. Acad. Sci. USA* (1995) 92:4299-4303.
Botto et al. "Amyloid deposition is delayed in mice with targeted deletion of the serum amyloid P component gene" *Nature Med.* (1997) 3(8):855-859.
Thompson et al. "The Structures of Crystalline Complexes of Human Serum Amyloid P Component with its Carbohydrate Ligand, The Cyclic Pyruvate Acetal of Galactose" *J. Mol. Biol.* (2002) 320:1081-1086.
Gelas et al. "Recherches Dans La Série Des Acetals Cycliques" *Carbohydrate Res.* (1973) 30:21-32.
Pepys et al. "Targeted pharmacological depletion of serum amyloid P component for treatment of human amyloidosis" *Nature* (2002) 417:254-259.

*Primary Examiner*—Patrick T Lewis
(74) *Attorney, Agent, or Firm*—Foley & Lardner LLP

(57) ABSTRACT

Novel glycerol cyclic pyruvate derivates were prepared and demonstrated to inhibit the binding of an immobilized D-proline derivative to serum amyloid P component (SAP) have been prepared. As such, the compounds of the invention are useful for treating amyloidosis and diseases associated with amyloidosis, for example Alzheimer&supl;s disease and maturity onset diabetes mellitus.

34 Claims, 3 Drawing Sheets

MULTIVALENT INHIBITORS OF SERUM AMYLOID P COMPONENT

FIELD OF THE INVENTION

The present invention relates to new glycerol cyclic pyruvate derivatives and their use, in particular in the treatment or prevention of amyloidosis.

BACKGROUND OF THE INVENTION

Human serum amyloid P component (SAP) is a normal plasma protein that has been associated with amyloid fibrils in all types of amyloidosis. Amyloidosis is a disorder of protein metabolism in which normally soluble autologous proteins are deposited in tissues as abnormal insoluble fibrils that can cause structural and functional disruptions. Disorders most often associated with amyloidosis are Alzheimer's disease and maturity onset diabetes mellitus.

It has been shown that the calcium-dependent binding of SAP to amyloid fibrils in vitro protects those fibrils from proteolytic degradation by proteinases (Tennent, G. A. et al. Proc. Natl. Acad. Sci. USA. 1995, 92, 4299-4303). The participation of SAP in the pathogenesis of amyloidosis has also been confirmed in vivo (Botto, M. et al. Nature Med. 1997, 3, 855-859). It has been proposed that SAP is needed for amyloidogenesis, possibly to protect newly formed fibrils from proteolysis. If the binding of SAP to fibrils could be inhibited or reversed, the destruction of fibrils by, for example, macrophages and/or proteinases, may be allowed to proceed. Inhibition or reversal of calcium-dependent binding of SAP to amyloid fibrils (either newly synthesized or established flibrils) may therefore be used in the treatment of amyloidosis, for example in the treatment of Alzheimer's disease.

It has long been known that SAP binds to some bacterial and plant oligosaccharides in $Ca^{2+}$-dependent manner. Agarose is used as a matrix for affinity column purification of SAP. Some of these oligosaccharides contain cyclic pyruvate as a common fragment and the crystal structure of a complex of SAP and its smallest ligand containing a pyruvate, methyl 4,6-(1-carboxyethylidene)-β-D-galactoside 1 (often abbreviated as MOβDG) was recently reported (J. Mol. Biol., 2002, 320, 1081-1086). It was reported that the methyl group binds to a very small lipophilic pocket and the carboxylate coordinates with both $Ca^{2+}$-cations. Oxygen atoms of dioxane ring were engaged in hydrogen bonds with Asn 59 and Gln 148.

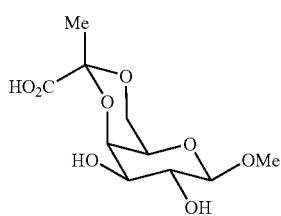

1

The preparation of the compound 2 has been previously reported (Carbohydrate Res. 1973, 30, 21-32) but no reference to its use as a SAP inhibitor was made.

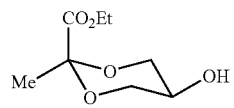

2

Certain D-proline analogs of have been prepared and shown to inhibit the binding of SAP to human amyloid Aβ (1-42) fibrils and therefore may be used in the treatment or prevention of all forms of local and systemic amyloidosis (Hertel, C. et al. U.S. Pat. No. 6,103,910; Hertel, C. et al. U.S. Pat. No. 6,262,089; Pepys, M. B. et al. Nature, 2002, 417, 254-259). D-Proline mimics MOβDG and binds to the same $Ca^{2+}$-dependent binding site on the SAP surface.

There remains a need for effective inhibitors of the binding of SAP to human amyloid fibrils for the use in the treatment or prevention of amyloidosis.

SUMMARY OF THE INVENTION

The present inventors have found that the cyclic pyruvate ketal is the only structural feature important for molecular recognition between SAP and $Ca^{2+}$-dependent ligands. Although ligand 1 (see above) makes two contacts with SAP outside of the cyclic pyruvate fragment (3-OH with Gln 148 and 1-OH with Lys 79) and the latter H-bond was speculated to play a major role in SAP-1 binding specificity, it has been found that, in fact, these additional hydrogen bonds do not contribute significantly to the binding energy and are not important for specificity of the molecular recognition (See the crystal structure in FIGS. 2 and 3 and Example 68).

Accordingly, the present invention relates to compounds of Formula I:

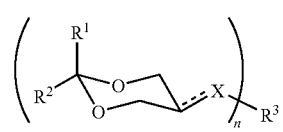

I wherein
$R^1$ is selected from the group consisting of $CO_2H$, $CO_2C_{1-6}$alkyl and tetrazole;
$R^2$ is $C_{1-6}$alkyl;
᎓᎓᎓ is a single or a double bond such that when ᎓᎓᎓ is a single bond, X is selected from the group consisting of O, S, NH, $CH_2$, OC(O) and O(CO)NH, and when ᎓᎓᎓ is a double bond, X is selected from the group consisting of O, S, N and CH;
$R^3$ is selected from the group consisting of H, a small oligosaccharide or saccharide, a small peptide, a small oligocarbamate, $(LA)_m$, $(LA)_m$MFC and when ᎓᎓᎓ is a double bond and X is O or S, $R^3$ is non-existent;
n is an integer between, and including, 1 and 20;
m is an integer between and including, 1 and 20;
LA is a linker arm selected from the group consisting of arylene, a peptide chain, oligocarbamate, $C_{2-60}$ straight, branched or cyclic alkylene and $C_{2-60}$ straight, branched or cyclic alkenylene, wherein in both alkylene and alkenylene, one or more of the carbons may optionally be replaced with an O, S, N and/or $NR^6$ and optionally interrupted by arylene, and the linker arms can optionally be functionalized at one or more positions with a functional group selected from the group consisting of aryl, heteroaryl, heterocyclo, $C_{3-8}$cycloalkyl, OH, O-aryl, O-heteroaryl O-heterocyclo, O—$C_{3-8}$cycloalkyl and O—$C_{1-6}$alkyleneheterocyclo, wherein the aryl, heteroaryl, cycloalkyl and heterocyclo may each be independently optionally substituted;

$R^6$ is selected from the group consisting of H and $C_{1-6}$alkyl;

MFC is a multifunctional core group; and pharmaceutically acceptable salts, hydrates, solvates and prodrugs thereof.

Also included within the scope of the present invention is a pharmaceutical composition comprising a compound of Formula I and a pharmaceutically acceptable carrier.

The present invention further includes a method of treating or preventing amyloidosis comprising administering an effective amount of a compound of Formula I to an animal in need thereof. Further, the invention includes the use of a compound of Formula I for treating or preventing amyloidosis and the use of a compound of Formula I for preparing a medicament for treating or preventing amyloidosis.

Also included within the scope of the present invention is a method of treating diseases associated with amyloidosis comprising administering an effective amount of a compound of Formula I to an animal in need thereof. Further, the invention includes the use of a compound of Formula I for treating diseases associated with amyloidosis and the use of a compound of Formula I for preparing a medicament treating diseases associated with amyloidosis.

Compounds of Formula I have advantages over native (compound 1) and other synthetic SAP ligands (for example the D-proline analogs described in Hertel, C. et al. ibid) when used as a specific recognition fragment for designed SAP inhibitors. These advantages include:

1. Ease of synthetic accessibility as they are derived from glycerol and a pyruvate ester, both are inexpensive products of the food industry;
2. Simpler stereochemistry; and
3. Smaller molecular weight when compared to with compound 1, glycosaminoglycans, DNA, RNA and other native ligands.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWING

The invention will now be described in greater detail with reference to the following drawing in which.

Figure 1:
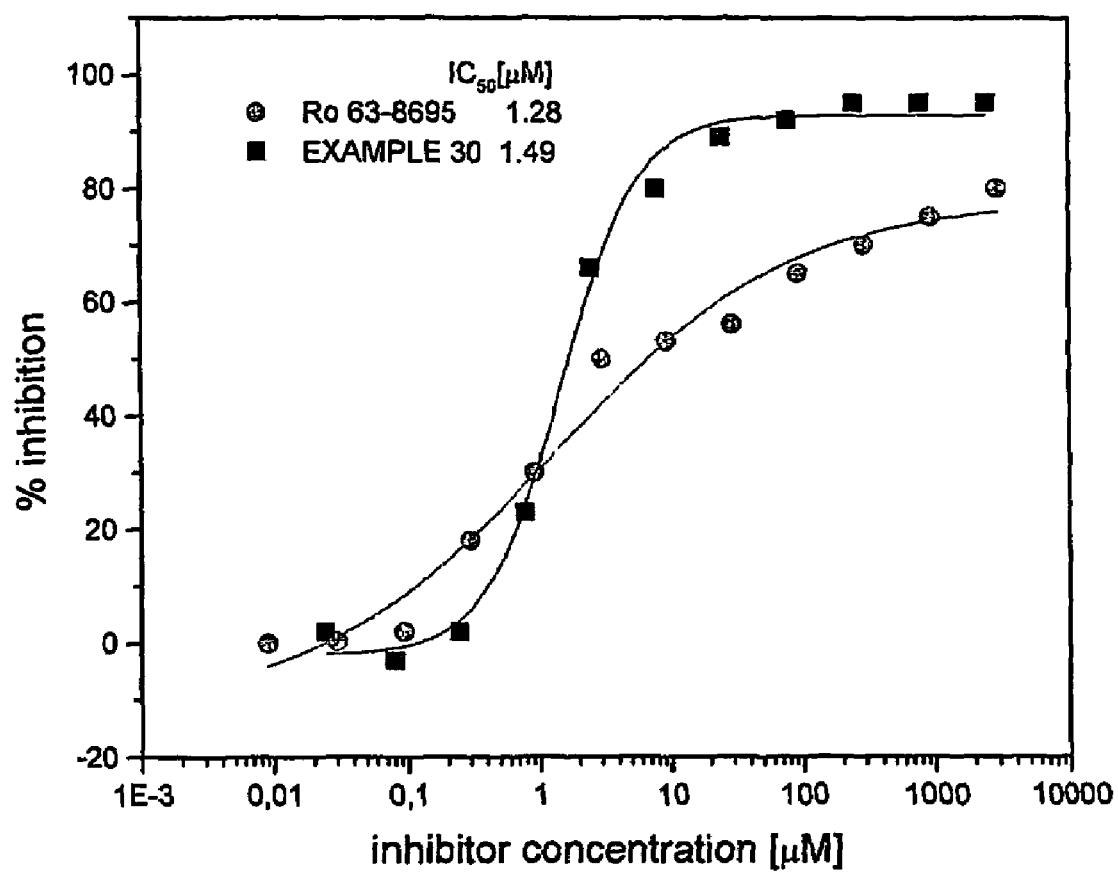
FIG. 1 is a representative graph showing the results of the solid-phase assays for the compound Iv and a Hoffman La Roche compound Ro 63-8695.
Figure 2:
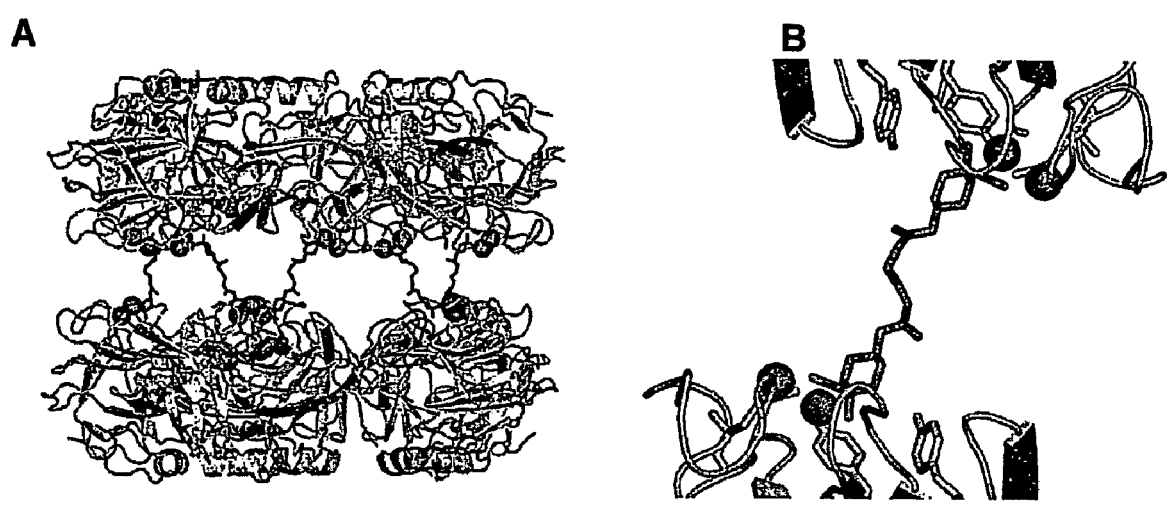
FIG. 2 shows (A) Ribbon diagram showing the formation of a decamer by the binding of five bivalent molecules of Compound Ib to two pentamers of SAP; (B) Detail view of Compound Ib interacting with the calcium binding sites from two different SAP pentamers. The protein structure is drawn as a ribbon, with stick representations of residues 64, 74 and 148 at the active sites. Calcium is represented by a solid sphere.
Figure 3:
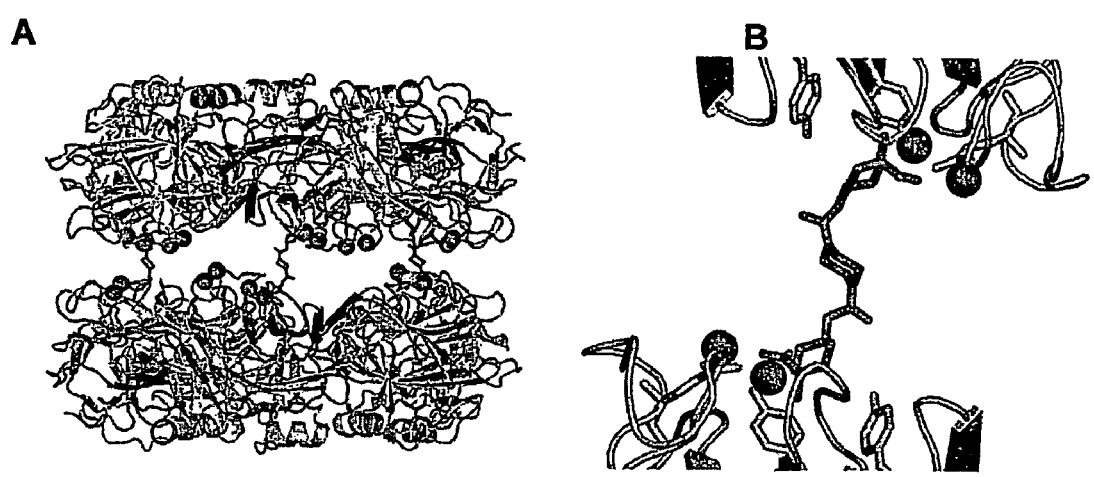
FIG. 3 shows (A) Ribbon diagram showing the formation of a decamer by the binding of five bivalent molecules of Compound II to two pentamers of SAP; (B) Detail view of Compound II interacting with the calcium binding sites from two different SAP pentamers. The protein structure is drawn as a ribbon, with stick representations of residues 64, 74 and 148 at the active sites. Calcium is represented by a solid sphere.

DETAILED DESCRIPTION OF THE INVENTION (i) Compounds

Novel compounds showing inhibition of the binding of an immobilized D-proline derivative to serum amyloid P component (SAP) have been prepared. As such, the compounds of the invention are useful for treating amyloidosis and diseases associated with amyloidosis, for example Alzheimer's disease and maturity onset diabetes mellitus.

Accordingly, the present invention relates to compounds of Formula I:

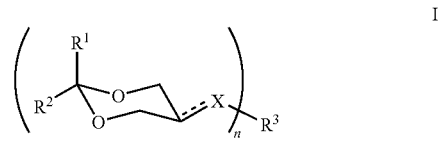

I wherein $R^1$ is selected from the group consisting of $CO_2H$, $CO_2C_{1-6}$alkyl and tetrazole;

$R^2$ is $C_{1-6}$alkyl;

⁃⁃⁃⁃⁃ is a single or a double bond such that when ⁃⁃⁃⁃⁃ is a single bond, X is selected from the group consisting of O, S, NH, $CH_2$, OC(O) and O(CO)NH, and when ⁃⁃⁃⁃⁃ is a double bond, X is selected from the group consisting of O, S, N and CH:

$R^3$ is selected from the group consisting of H, a small oligosaccharide or saccharide, a small peptide, a small oligocarbamate, $(LA)_m$, $(LA)_m$MFC and when ⁃⁃⁃⁃⁃ is a double bond and X is O or S, $R^3$ is non-existent;

n is an integer between, and including, 1 and 20;

m is an integer between and including, 1 and 20;

LA is a linker arm selected from the group consisting of arylene, a peptide chain, oligocarbamate, $C_{2-60}$ straight, branched or cyclic alkylene and $C_{2-60}$ straight, branched or cyclic alkenylene, wherein in both alkylene and alkenylene, one or more of the carbons may optionally be replaced with an O, S, N and/or $NR^6$ and optionally interrupted by arylene, and the linker arms can optionally be functionalized at one or more positions with a group selected from aryl, heteroaryl, heterocyclo, $C_{3-8}$cycloalkyl, OH, O-aryl, O-heteroaryl O-heterocyclo, O—$C_{3-8}$cycloalkyl and O—$C_{1-6}$alkyleneheterocyclo, wherein the aryl, heteroaryl, cycloalkyl and heterocyclo may each be independently optionally substituted;

$R^6$ is selected from the group consisting of H and $C_{1-6}$alkyl;

MFC is a multifunctional core group; and pharmaceutically acceptable salts, hydrates, solvates and prodrugs thereof.

Embodiments of the invention are exemplified, but not limited to, compounds of Formula I-A, I-B, I-C and I-D as shown below:

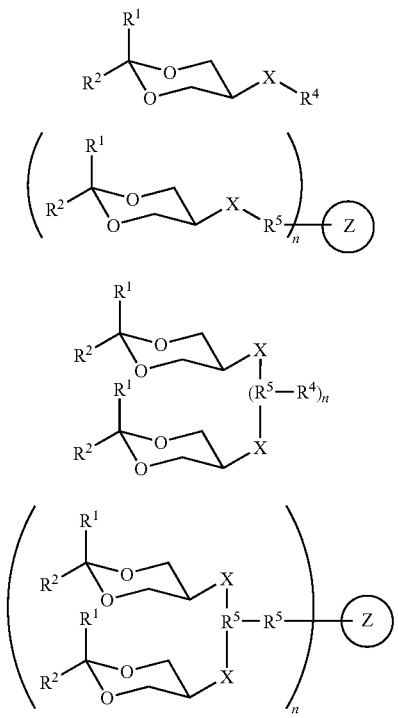

I-A

I-B

I-C

I-D wherein:
R$^1$ is selected from the group consisting of CO$_2$H, CO$_2$C$_{1-6}$alkyl and tetrazole;
R$^2$ is C$_{1-6}$alkyl;
each X is independently selected from the group consisting of O, S, NH, CH$_2$, OC(O) and O(CO)NH;
each n is independently an integer between, and including, 1-20;
each R$^4$ is independently selected from the group consisting of H, a small oligosaccharide or saccharide, a small peptide and a small oligocarbamate;
each R$^5$ is a linker group independently selected from the group consisting of arylene, a peptide chain, oligocarbamate, C$_{2-60}$ straight, branched or cyclic alkylene, and C$_{2-60}$ straight, branched or cyclic alkenylene, wherein in both alkylene and alkenylene, one or more of the carbons may optionally be replaced with an O, S, N and/or NR$^6$ and optionally interrupted by arylene, and the linker arms can optionally be functionalized at one or more positions with a group selected from aryl, heteroaryl, heterocyclo, C$_{3-8}$cycloalkyl, OH, O-aryl, O-heteroaryl O-heterocyclo, O—C$_{3-8}$cycloalkyl and O—C$_{1-6}$alkyleneheterocyclo, wherein the aryl, heteroaryl, cycloalkyl and heterocyclo groups may each be independently optionally substituted;
R$^6$ is selected from the group consisting of H and C$_{1-6}$alkyl;
each Z is, independently, a multifunctional core (MFC) group, and
pharmaceutically acceptable salts, hydrates, solvates and prodrugs thereof.

In embodiments of the invention, R$^1$ is CO$_2$H, CO$_2$Me or CO$_2$Et, specifically CO$_2$H.

In other embodiments of the invention, R$^2$ is C$_{1-4}$alkyl, specifically methyl or ethyl, more specifically methyl.

In further embodiments of the invention X is selected from the group consisting of O, S, OC(O) and O(CO)NH.

In still further embodiments of the invention the compound of the invention is selected from a compound of Formula I-B, I-C and I-D.

The linker arms or linker groups (R$^5$), in an embodiment of the invention, are selected from the group consisting of phenylene, an amino acid, such as alanine, C$_{2-30}$ straight, branched or cyclic alkylene, and C$_{2-30}$ straight, branched or cyclic alkenylene, wherein in both alkylene and alkenylene, one or more of the carbons may optionally be replaced with an O and/or S and optionally interrupted by arylene, and the linker arms or groups can optionally be functionalized at one or more positions with a group selected from phenyl, OH, O-phenyl and O-saccharide, wherein the phenyl group is optionally substituted. In further embodiments of the invention, the linker arms or groups are selected from 1,4-phenylene; 1,3-phenylene; 1,2-phenylene; C$_{2-20}$alkylene optionally substituted with OH and a saccharide, specifically β-D-glucopyranosyl, and one or more of the carbons may optionally be replaced with an O and/or S; —(CH$_2$)$_p$—Ph—(CH$_2$)$_p$ wherein p is an integer between, and including, 1-6, specifically, 1-4, more specifically 1;
—(CH$_2$)$_p$—CH=CH—(CH$_2$)$_p$ wherein p is an integer between, and including, 1-6, specifically, 1-4, more specifically 1;

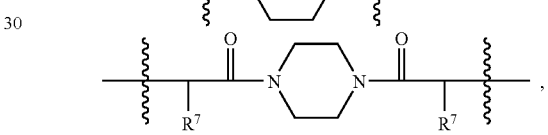

wherein R$^7$ is the sidechain of an amino acid, specifically CH$_3$, CH$_2$Ph, CH(CH$_3$)$_2$, more specifically CH$_3$.

The term multifunctional core group includes biocompatible multifunctional molecules which include between three and 20 reactive sites which can be used to couple with a linker arm. As used herein, "reactive site" refers to a site which includes a nucleophile or a leaving group such that a linker arm which includes a leaving group or nucleophile, respectively, can be coupled to the core molecule. As an example, a core molecule including a halide can be linked to a linker arm including a hydroxy group via an etherification reaction, or to a linker arm including an amine via nucleophilic displacement of the halide. Examples of suitable multifunctional core molecules include sugars, such as mono-, di- and tri-saccharides, polyhydroxy compounds such as penta-erithritol, short chain polylysines, polysubstituted aromatics, cycloalkanes, polyacrylamides, cyclodextrins, phthalocyanins, mono- and oligosaccharides, inositols, and alditols. Such multifunctional core molecules are described in the inventors' U.S. Pat. Nos. 5,962,423 and 6,310,043, the contents of which are incorporated by reference in their entirety. Other examples of multifunctional core groups include, but are not limited to, silver and gold nanoparticles. In embodiments of the invention the MFC group is an organic polyol. By "polyol", it is meant that the compound has more than one alcohol group for attachment (binding) to the linker group. Each linker group has bound to the other end the glycerol cyclic pyruvate group. The organic portion of the polyol may have any suitable structure ranging from straight and branched chain alkyl and alkenyl groups, to cyclic and aromatic groups. It is an embodiment of the invention that the polyol is derived from natural sources. Particular examples of polyols include, but are not limited to, saccharides (including monosaccharides, disaccharides and trisaccharides), glycerol, propylene glycol and trimethylene glycol. The saccharide may be any aldo- or keto-triose, pentose, hexose or heptose, in either the open-chained or cyclic form. Examples of monosaccharides that may be used in the present invention include, but are not limited to, allose, altrose, glucose, mannose, gulose, idose, galactose, talose, ribose, arabinose, xylose, lyxose, threose, erythrose, glyceraldehydes, sorbose, fructose, dextrose, levulose and their reduced forms such as xylitol and sorbitol. Examples of disaccharides that may be used in the present invention include, but are not limited to, lactose, sucrose, threhalose, cellobiose and maltose.

In specific embodiments of the invention, the compounds of Formula I include:

Bis-1,2-{[(Z)-2-ethoxycarbonyl-2-methyl-[1,3]dioxane]-5-yloxycarbamoyl}-ethane (Ia)
Bis-1,2-{[(Z)-2-carboxy-2-methyl-[1,3]dioxane]-5-yloxycarbamoyl}-ethane (Ib)
Bis-1,3-[((Z)-2-methoxycarbonyl-2-methyl-[1,3]dioxane)-5-yloxycarbamoyl]-propane (Ic)
Bis-1,3-[((Z)-2-carboxy-2-methyl-[1,3]dioxane)-5-yloxycarbamoyl]-propane (Id)
Bis-1,4-{[(Z)-2-ethoxycarbonyl-2-methyl-[1,3]dioxane]-5-yloxycarbamoyl}-butane (Ie)
Bis-1,4-{[(Z)-2-carboxy-2-methyl-[1,3]-dioxane]-5-yloxycarbamoyl}-butane (If)
Bis-1,5-{[(Z)-ethoxycarbonyl-2-methyl-[1,3]dioxane]-5-yloxycarbamoyl}-pentane (Ig)
Bis-1,5-{[(Z)-2-carboxy-2-methyl-[1,3]dioxane]-5-yloxycarbamoyl}-pentane (Ih)
Bis-1,6-{[(Z)-2-methoxycarbonyl-2-methyl-[1,3]dioxane]-5-yloxycarbamoyl}-hexane (Ii)
Bis-1,6-{[(Z)-2-carboxy-2-methyl-[1,3]dioxane]-5-yloxycarbamoyl}-hexane (Ij)
Bis-N,N-{[(Z)-2-ethoxycarbonyl-2-methyl-[1,3]dioxane]-5-yloxycarbonyl}-piperazine (Ik)
Bis-N,N-{[(Z)-2-carboxy-2-methyl-[1,3]dioxane]-5-yloxycarbonyl}-piperazine (Il)
Bis-N,N-{[(Z)-2-ethoxycarbonyl-2-methyl-[1,3]dioxane]-5-yloxycarbonyl-L-alanylo}-piperazine (Im)
Bis-N,N-{[(Z)-2-carboxy-2-methyl-[1,3]dioxane)-5-yloxycarbonyl-L-alanylo]-piperazine (In)
Bis-1,3-[((Z)-2-ethoxycarbonyl-2-methyl-[1,3]dioxane)-5-yloxycarbonyl]-propan-2-ol (Io)
Bis-1,3-{[(Z)-2-ethoxycarbonyl-2-methyl-[1,3]dioxane)-5-yloxycarbamoyl]-2-O-(2,3,4,6-tetra-O-acetylo-b-D-glucopyranozylo)-propan-2-ol (Ip)
Bis-1,3-{[(Z)-2-carboxy-2-methyl-1,3-dioxane)-5-yloxycarbamoyl]-2-O-(β-D-glucopyranozylo)-propan-2-ol (Iq)
Bis-1,4-[((Z)-2-carboxy-2-methyl-[1,3]dioxane)-5-yloxymethyl]-benzene (Ir)
Bis-1,3-[((Z)-2-carboxy-2-methyl-[1,3]dioxane)-5-yloxymethyl]-benzene (Is)
Bis-1,2-[((Z)-2-carboxy-2-methyl-[1,3]dioxane)-5-yloxymethyl]-benzene (It)
Bis-1,4-[((Z)-2-carboxy-2-methyl-1,3-dioxane)-5-yloxymethyl]-but-2-ene (Iu)
Bis-1,6-[((Z)-2-carboxy-2-methyl-[1,3]dioxane)-5-yloxy]-hexane (Iv)
Bis-1,3-[((E)-2-carboxy-2-methyl-[1,3]dioxane)-5-ylthio]-2-hydroxy-propane (Iw)
Bis-1,6-[((E)-2-carboxy-2-methyl-[1,3]dioxane)-5-ylthio]-hexane (Ix)
Bis-1,4-[((E)-2-carboxy-2-methyl-[1,3]dioxane)-5-ylthio]-but-2-ene (Iy)
Bis-1,4-[((E)-2-carboxy-2-methyl-[1,3]dioxane)-5-thiomethyl]-benzene (Iz)
5,9-Di-{[((Z)-2-carboxy-2-methyl-[1,3]dioxane)-5-yloxy]methyl}-2,12-di-hydroxy-1-mercapto-4,10,18,21,24,27,30,33,36-nona-oxa-7,14-di-thia-nonatriacontane (Ia')
1,11-Di-[((Z)-2-carboxy-2-methyl-[1,3]dioxane)-5-yloxy]-6-hydroxy-4,8-di-thia-undecane (Ib')
1,1,37,37-Tetra-{5-[((Z)-2-carboxy-2-methyl-[1,3]dioxane)-5-yloxy]-2-thia-pentyl}4,34-di-hydroxy-2,10,13,16,19,22,25,28,36-nona-oxa-6,32-di-thia-heptatriacontane (Ic')
Decamer 1 (Id')
Bis-1,3-[((Z)-2-methoxycarbonyl-2-methyl-[1,3]dioxane)-5-yloxycarbonyl]-propan-2-ol (Ie')
Decamer 2 (If)

and pharmaceutically acceptable salts, hydrates, solvates and prodrugs thereof.

The term "aryl" as used herein means unsubstituted or substituted mono- or bicyclic aromatic groups containing from 6 to 14 carbon atoms and includes phenyl and naphthyl and the like.

The term "heteroaryl" as used herein means unsubstituted or substituted mono- or bicyclic heteroaromatic groups containing from 5 to 14 carbon atoms, of which 1-3 atoms may be a heteroatom selected from the group consisting of S, O and N, and includes furanyl, thienyl, pyrrolo, pyridyl, indolo, benzofuranyl and the like.

The term heterocyclo as used herein means unsubstituted or substituted non-aromatic mono- or bicyclic heterocyclic groups containing from 3 to 10 carbon atoms, of which 1-3 atoms may be a heteroatom selected from the group consisting of S, O and N, and includes piperidinyl, tetrahydrofuranyl, pyrrolidinyl, saccharides and the like.

Simple saccharides are also known as carbohydrates or sugars. The saccaharide may be any aldo- or keto-triose, pentose, hexose or heptose, in either the open-chained or cyclic form. Examples of saccharides that may be used in the present invention include, but are not limited to, allose, altrose, glucose, mannose, gulose, idose, galactose, talose, ribose, arabinose, xylose, lyxose, threose, erythrose, glyceraldehydes, sorbose, fructose, dextrose, levulose and sorbitol.

When a cyclic group, such as aryl, heteroaryl and heterocyclo, is substituted the substituents may include 1-5, suitably 1-3, groups independently selected from $C_{1-4}$alkyl, $C_{2-4}$alkenyl $OC_{1-4}$alkyl, $OC_{2-4}$alkenyl, $CF_3$, $OCF_3$, OH, halo, cyano, nitro, $NH_2$, $NHC_{1-4}$alkyl and $N(C_{1-4}$alkyl$)(C_{1-4}$alkyl$)$.

As to any of the above groups that contain 1 or more substituents, it is understood, of course, that such groups do not contain any substitution or substitution patterns which are sterically impractical and/or synthetically non-feasible.

The term "small" in reference to "small peptide", "small oligosaccharide", "small oligocarbamate" and "small molecule which binds to the SAP surface adjacent to a $Ca^{2+}$-dependent binding site" refers to any such molecule having a molecular weight that is less than about 500 Da.

The term "oligocarbamate" as used herein refers to a peptide mimetic group in which the peptide linkage is replaced with a carbamate.

The term "$C_{1-n}$alkyl" as used herein means straight and/or branched chain, saturated alkyl groups containing from one to "n" carbon atoms and includes methyl, ethyl, propyl, isopropyl, s-butyl, t-butyl, neopentyl, and the like.

The term "$C_{2-n}$alkenyl" as used herein means straight and/or branched chain, unsaturated alkyl groups containing from two to "n" carbon atoms and at least one double bond and includes vinyl, allyl, butenyl and the like.

The term "halo" as used herein means halogen and includes chloro, flouro, bromo and iodo.

The term "solvate" as used herein means a compound wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "animal" as used herein includes all members of the animal kingdom including human. The animal is preferably a human.

The term "pharmaceutically acceptable" means compatible with the treatment of animals, including humans.

The term "pharmaceutically acceptable salt" means an acid addition salt or a basic addition salt which is suitable for or compatible with the treatment of animals, including humans.

The term "pharmaceutically acceptable acid addition salt" as used herein means any non-toxic organic or inorganic salt of any base compound of Formula I, or any of their intermediates. Basic compounds that may form an acid addition salt include, for example, those having a basic nitrogen. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of a compound are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds for laboratory use, or for subsequent conversion to a pharmaceutically acceptable acid addition salt.

The term "pharmaceutically acceptable basic addition salt" as used herein means any non-toxic organic or inorganic base addition salt of any acid compound of Formula I, or any of their intermediates. Acidic compounds that may form a basic addition salt include, for example, those having a carboxylate (C(O)OH) group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds, for laboratory use, or for subsequent conversion to a pharmaceutically acceptable acid addition salt.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that inhibits amyloidosis, an effective amount of an agent is, for example, an amount sufficient to achieve such inhibition of amyloidosis as compared to the response obtained without administration of the agent.

As used herein, and as well understood in the art, the term "treat" "treating" and/or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

To "inhibit" or "suppress" or "reduce" a function or activity, such as amyloidosis, is to reduce the function or activity when compared to otherwise same conditions except for a condition or parameter of interest, or alternatively, as compared to another conditions.

Compounds of Formula I may be prepared as described herein using chemistries known to those skilled in the art. In some cases the chemistries outlined herein may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of Formula I will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of Formula I may be, for example, conventional esters formed with available hydroxy, thiol, amino or carboxyl group. Some common esters which have been utilized as prodrugs are phenyl esters, aliphatic $(C_1\text{-}C_{24})$ esters, acyloxymethyl esters, carbamates and amino acid esters. Specific prodrugs include phenyl esters, aliphatic $(C_1\text{-}C_{24})$ esters, acyloxymethyl esters, carbamates and amino acid esters of the compounds of Formula I wherein $R^1$ is $CO_2H$. In embodiments of the invention, a prodrug of the compounds of the Formula I include the methyl and ethyl esters (i.e. $R^1$ is $CO_2Et$ or $CO_2Me$)

A radiolabeled compound of Formula I may be prepared using standard methods known in the art. For example, tritium may be incorporated into a compound using standard techniques, for example by hydrogenation of a suitable precursor to a compound using tritium gas and a catalyst. Alternatively, a compound containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine)palladium(0) in an inert solvent, such as dioxane, and at elevated temperatures, suitably 50-100° C.

(ii) Uses

As hereinbefore mentioned, novel compounds of the Formula I have been prepared. Accordingly, the present invention includes all uses of these compounds including their use in therapeutic methods and compositions for inhibiting amyloidosis, their use in diagnostic assays and their use as research tools and as starting materials and/or intermediates in the preparation of other chemical entities.

Compounds of Formula I, as inhibitors of the interaction of SAP and the abnormal insoluble vascular and cerebrovascular deposits known as amyloids, are useful for the treatment or prevention of all forms of central and systemic amyloidosis. The most common disorders associated with amyloidosis are Alzheimer's disease (AD), maturity onset diabetes mellitus, or amyloidosis as a significant cause of non-ischaemic heart failure, as complication of long term haemodialysis in renal failure, as complication of monoclonal gammopathies, from chronic inflammatory disorders, from chronic infections or from certain types of cancer. Furthermore, amyloidosis comprises many different diseases such as forms of hereditary amyloidosis most common familial amyloid polyneuropathy (FAP), scrapie and Kreuzfeld-Jakob disease. The common pathological feature is extracellular deposition of so called amyloid proteins in β-structured fibers and the same staining characteristics.

Accordingly, the present invention further includes a method of treating or preventing amyloidosis comprising administering an effective amount of a compound of Formula I to an animal in need thereof. Further, the invention includes the use of a compound of Formula I for treating or preventing amyloidosis and the use of a compound of Formula I for preparing a medicament for treating or preventing amyloidosis.

Also included within the scope of the present invention is a method of treating diseases associated with amyloidosis comprising administering an effective amount of a compound of Formula I to an animal in need thereof. Further, the invention includes the use of a compound of Formula I for treating diseases associated with amyloidosis and the use of a compound of Formula I for preparing a medicament treating diseases associated with amyloidosis.

One skilled in the art can determine which compounds of Formula I would have therapeutic utility, for example, in inhibiting amyloidosis. For example, compounds may be examined for their efficacy in inhibiting the binding of SAP to an immobilized D-proline derivative as described in Example 27 herein. The compounds may also be tested for their efficacy in inhibiting the binding of SAP to amyloid fibrils as described in Pepys, M. B. and Blundell, T. L., U.S. Pat. No. 6,126,918.

The compounds of Formula I are preferably formulated into pharmaceutical compositions for administration to human subjects in a biologically compatible form suitable for administration in vivo. Accordingly, in another aspect, the present invention provides a pharmaceutical composition comprising a compound of Formula I, or a pharmaceutically acceptable salt, hydrate, solvate or prodrug thereof, in admixture with a suitable diluent or carrier.

The compositions containing the compounds of Formula I can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of Formula I may be used pharmaceutically in the form of the free base, in the form of salts, solvates and as hydrates. All forms are within the scope of the invention. Acid and basic addition salts may be formed with the compounds for use as sources of the free base form, even if the particular salt per se is desired only as an intermediate product as, for example, when the salt is formed only for the purposes of purification and identification. All salts that can be formed with the compounds of the invention are therefore within the scope of the present invention.

In accordance with the methods of the invention, the described compounds of Formula I, or salts, solvates, hydrates or prodrugs thereof, may be administered to a patient in a variety of forms depending on the selected route of administration, as will be understood by those skilled in the art. The compounds of Formula I may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of Formula I may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of Formula I may be incorporated with excipient and used in the form of ingestible tablets, buccal tablets, troches, capsules, elixirs, suspensions, syrups, wafers, and the like.

A compound of Formula I may also be administered parenterally. Solutions of a compound of Formula I can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of Formula I, or salts, solvates, hydrates or prodrugs thereof, may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds of Formula I, and/or compositions comprising the same, can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of Formula I may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

The compounds of Formula I, or salts, solvates, hydrates or prodrugs thereof, can be used alone or in combination with other agents that inhibit amyloidosis or in combination with other types of treatment (which may or may not inhibit amyloidosis) for diseases and disorders that are associated with amyloidosis, for example Alzheimer's disease and maturity onset diabetes mellitus.

In diagnostic assays the compounds of Formula I may be useful in identifying or detecting an amyloidosis. In such an embodiment, the compounds may be radiolabelled (as hereinbefore described) and contacted with a population of cells. The presence of the radiolabelled on the cells may indicate an amyloidosis. In screening assays, the compounds of Formula I may be used to identify other compounds that inhibit. In such assays, the compounds may also be radiolabelled.

The following non-limiting examples are illustrative of the present invention:

EXAMPLES

Example 1

(Z)-2-Methyl-2-methoxycarbonyl-5-(p-nitro-phenoxycarbonyloxy))-[1,3]dioxane (3)

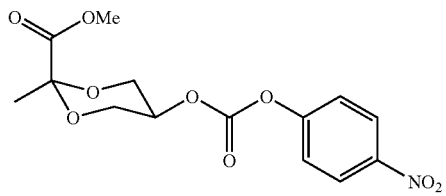

To a solution of 1-methyl-2,5,7-trioxa-bicyclo[2.2.2]octan-6-one (4.0 g; 27.7 mmol) in dry methanol (30 ml) a solution of 1 M NaOMe (1 ml) was added and the mixture was kept at room temperature for 1 h. Then it was neutralized with Dowex (H⁺) resin to pH 7, filtered and concentrated. The resulting oily syrup was dissolved in dry DCM (30 ml) and p-nitrophenyl chloroformate (6.67 g; 33 mmol) was added followed by dry pyridine (5.2 g; 66 mmol). The mixture was stirred for 2 h at room temperature then diluted with DCM, washed with brine, concentrated and co-evaporated with toluene. Chromatography of the residue on silica gel with toluene-ethyl acetate (10:1-17:3) provided the title compound 3 as a syrup, which later slowly crystallized (5.94 g; 63%). $^1$H-NMR (CDCl$_3$): δ 8.28-8.24 (m, 2H, arom.), 7.36-7.33 (m, 2H, arom.), 4.94-4.89 (m, 1H, H-5), 4.26-4.23 (m, 2H, H-4e, H-6e), 3.85 (s, 3H, OCH$_3$), 3.78-3.75 (m, 2H, H-4a, H-6a), 1.55 (s, 3H, CH$_3$). Electrospray ionization MS m/z: 364 (M+Na).

Example 2

(Z)-2-Ethoxycarbonyl-2-methyl-5-(p-nitrophenoxycarbonyloxy)-[1,3]dioxane (4)

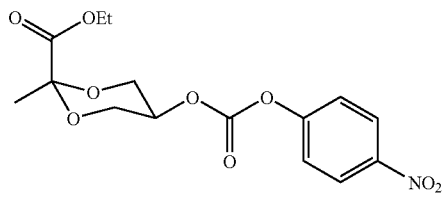

A solution of 1-methyl-2,5,7-trioxa-bicyclo[2.2.2]octan-6-one (9.14 g, 63.4 mmol) in anhydrous ethanol (80 ml) was treated with 1 M NaOEt (2 ml). The mixture was stirred at room temperature overnight then neutralized with Dowex (H⁺) resin, filtered and concentrated. The oily product was dissolved in dry DCM (70 ml) and p-nitrophenylchloroformate (15.35 g, 76.13 mmol) was added followed by dry pyridine (12 g, 152 mmol). After stirring at room temperature for 1 h the mixture was diluted with DCM, washed with brine, concentrated and chromatographed on silica gel with toluene-ethyl acetate (10:1) to provide an oily product which slowly crystallized to give compound 4 (14.9 g; 66%). $^1$H-NMR (CDCl$_3$): δ 8.28-8.24 (m, 2H, arom.), 7.37-7.33 (m, 2H, arom.), 4.94-4.89 (m, 1H, H-5), 4.31 (q, 1H, J=7.14 Hz, OCH$_2$), 4.26-4.22 (m, 2H, H-4e, H-6e), 3.78-3.74 (m, 2H, H-4a, H-6a), 1.54 (s, 3H, CH$_3$), 1.35 (t, 3H, CH$_3$). Electrospray ionization MS m/z: 376 (M+Na).

Example 3

Bis-1,2-{[(Z)-2-ethoxycarbonyl-2-methyl-[1,3]dioxane]-5-yloxycarbamoyl}-ethane (Ia)

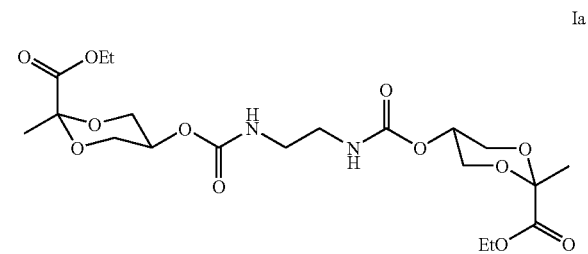

To a solution of ethylenediamine (44 mg, 0.72 mmol) and triethylamine (0.37 g, 3.6 mmol) in DCM (0.5 ml) a solution of (Z)-2-ethoxycarbonyl-2-methyl-5-(p-nitrophenoxycarbonyloxy)-[1,3]dioxane (0.64 mg, 1.8 mmol) in DCM (3.5 ml) was added and the mixture was stirred for 2 h at room temperature. The mixture was diluted with DCM, washed with aq. NaHCO$_3$, concentrated and chromatographed on silica gel with hexane-acetone (4:1-2:1) to give crystalline compound Ia (297 mg; 84%). $^1$H-NMR (CDCl$_3$): δ 5.08-5.00 (m, 2H, NH), 4.79 (tt, 2H, J$_{4e,5}$=J$_{5,6e}$=5.2 Hz, J$_{4e,5}$=J$_{5,6e}$=10.3 Hz, H-5), 4.29 (q, 4H, J=7.05 Hz, CH$_2$), 4.11 (dd, 4H, J$_{4a,4e}$=J$_{6a,6e}$=11.1 Hz, H-4e, H-6e), 3.57 (dd, 4 H, H-4a, H-6a), 3.28-3.22 (m, 4H, NCH$_2$), 1.50 (s, 6H, CH$_3$), 1.32 (t, 6H, CH$_3$). Electrospray ionization MS m/z: 515 (M+Na).

Example 4

Bis-1,2-{[(Z)-2-carboxy-2-methyl-[1,3]dioxane]-5-yloxycarbamoyl}-ethane (Ib)

Ib

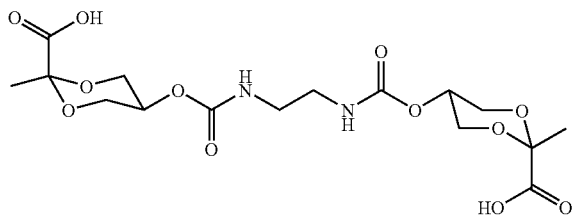

Bis-1,2-{[(Z)-2-ethoxycarbonyl-2-methyl-[1,3]dioxane]-5-yloxycarbamoyl}-ethane (50 mg, 0.1 mmol) was dissolved in methanol and treated with 2 M NaOH aqueous solution (0.2 ml). The mixture was kept at room temperature for 1 h then concentrated, dissolved in water and left overnight at room temperature. The mixture was acidified with Dowex (H$^+$) resin, filtered, concentrated and lyophilized to provide product Ib as a white foam. $^1$H-NMR (D$_2$O): δ 4.70-4.65 (m, 2H, H-5), 4.18-4.10 (m, 4H, H-4e, H-6e), 3.70-3.64 (m, 4H, H-4a, H-6a), 3.19 (s, 4H, NCH$_2$), 1.50 (s, 6H, CH$_3$). Electrospray ionization MS m/z: 503 (M+3Na-2H); 481 (M+2Na—H); 451 (M+Na).

Example 5

Bis-1,3-[((Z)-2-methoxycarbonyl-2-methyl-[1,3]dioxane)-5-yloxycarbamoyl]-propane (Ic)

Ic

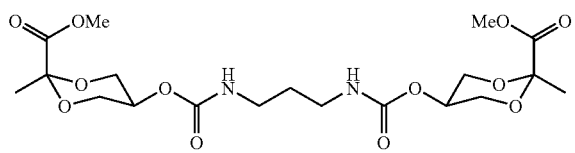

A solution of (Z)-2-methyl-2-methoxycarbonyl-5-(p-nitro-phenoxycarbonyloxy))-[1,3]dioxane (484 mg, 1.42 mmol) in DCM (2 ml) was added to a stirred solution of 1,3-diaminopropane (42 mg; 0.57 mmol) in DCM (0.5 ml) followed by triethylamine (0.29 g; 2.86 mmol). After stirring for 2 h at room temperature the mixture was concentrated and chromatographed on silica gel with hexane-acetone (4:1-2:1) to afford the title compound Ic as a colorless syrup (230 mg, 85%). $^1$H-NMR CDCl$_3$): δ 5.06-5.02 (m, 2H, NH), 4.79 (tt, 2H, J$_{4e,5}$=J$_{5,6e}$=5.2 Hz, J$_{4a,5}$=J$_{5,6a}$=9.4 Hz, H-5), 4.12 (dd, 4H, J$_{4e,4a}$=J$_{6e,6a}$=11.7 Hz, H-4e, H-6e), 3.82 (s, 6H, OCH$_3$), 3.56 (dd, 4H, H-4a, H-6a), 3.16 (dd, 4H, J 6.2 Hz, NCH$_2$), 1.60 (ddd, 4H, CH$_2$), 1.51 (s, 6H, CH$_3$). Electrospray ionization MS m/z: 501 (M+Na).

Example 6

Bis-1,3-[((Z)-2-carboxy-2-methyl-[1,3]dioxane)-5-yloxycarbamoyl]-propane (Id)

Id

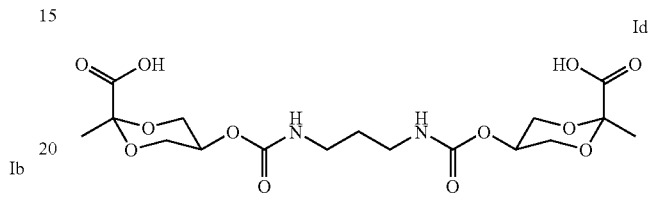

Bis-1,3-[((Z)-2-methoxycarbonyl-2-methyl-[1,3]dioxane)-5-yloxycarbamoyl]-propane (215 mg; 0.45 mmol) was treated with NaOH (43 mg, 4 eq.) in methanol-water solution. The solution was stirred at room temperature overnight, then neutralized with Dowex (H$^+$) resin, filtered, concentrated and purified on HPLC reverse-phase (C-8) column. The product was eluted with 100% water. Appropriate fractions were concentrated to provide the title compound Id as a white foam (168 mg; 83%). $^1$H-NMR (D$_2$O): δ 4.68 (dddd, 2H, J$_{4e,5}$=J$_{5,6e}$=4.8 Hz, J$_{4a,5}$=J$_{5,6a}$=8.9 Hz, H-5), 4.1 (dd, 4H, J$_{4e,4a}$=J$_{6e,6a}$=11.4 Hz, H-4, H-6), 3.64 (t, 4H, H-4a, H-6a), 3.12 (t, 4H, J 6.7 Hz, NCH$_2$), 1.64 (ddd, 2H, CH$_2$). Electrospray ionization MS m/z: 517.1 (M+3Na), 495.1 (M+2Na), 473.2 (M+Na), 451.2 (M+H).

Example 7

Bis-1,4-{[(Z)-2-ethoxycarbonyl-2-methyl-[1,3]dioxane]-5-yloxycarbamoyl}-butane (Ie)

Ie

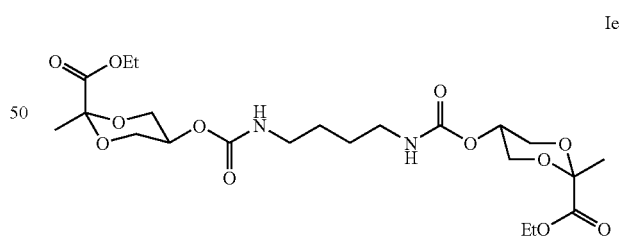

A solution of (Z)-2-ethoxycarbonyl-2-methyl-5-(p-nitrophenoxycarbonyloxy)-[1,3]dioxane (0.62 g, 1.81 mmol) in DCM (4 ml) was combined with a solution of 1,4-diaminobutane (64 mg, 0.72 mmol) in DCM (1 ml) and triethylamine (0.37 g, 3.6 mmol) was added. After stirring for 2 h at room temperature the mixture was concentrated. Chromatography on silica gel with hexane-acetone (4:1-2:1) afforded crystalline product Ie (0.38 g, 100%). $^1$H-NMR (CDCl$_3$): δ 4.82-4.77 (tt, 2H, J$_{4e,5}$=J$_{5,6e}$=5.25 Hz, H-5), 4.71-4.68 (m, 2H, NH), 4.28 (q, 4H, J 7.14, CH$_2$), 4.12 (dd, 4H, J$_{4a,4e}$=J$_{6a,6e}$=11.7 Hz, H-4e, H-6e), 3.56 (dd, 4H, H-4a, H-6a), 3.16-

3.10 (m, 4H, NCH$_2$), 1.50 (s, 6H, CH$_3$), 1.48-1.44 (m, 4H, CH$_2$), 1.32 (t, 6H, CH$_3$). Electrospray ionization MS m/z: 543 (M+Na).

Example 8

Bis-1,4-{[(Z)-2-carboxy-2-methyl-[1,3]-dioxane]-5-yloxycarbamoyl}-butane (If)

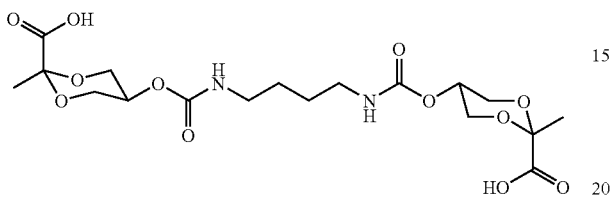

Bis-1,4-{[(Z)-2-ethoxycarbonyl-2-methyl-[1,3]dioxane]-5-yloxycarbamoyl}-butane (55 mg, 0.1 mmol) was dissolved in MeOH-DCM and treated with 2 M aqueous NaOH (0.2 ml). The solution was stirred at room temperature overnight, then neutralized with Dowex (H$^+$) resin, filtered, concentrated and purified on HPLC reverse-phase (C-8) column. The product was eluted with 100% water to afford the product If (39 mg, 84%). $^1$H-NMR (D$_2$O): δ 4.75-4.65 (m, 2H, H-5), 4.14 (dd, 4H, J$_{4e,5}$=J$_{5,6e}$=4.3 Hz, J$_{4a,4e}$=J$_{6a,6e}$=11.7 Hz, H-4e, H-6e), 3.68 (dd, 4H, J$_{4a,5}$=J$_{5,6a}$=8.7 Hz, H-4a, H-6a), 3.2 (broad s, 4H, NCH$_2$), 1.52 (s, 6H, CH$_3$), 1.47 (broad s, 4H, CH$_2$). Electrospray ionization MS m/z: 531 (M+3Na-2H); 509 (M+2Na—H); 487 (M+Na).

Example 9

Bis-1,5-{[(Z)-ethoxycarbonyl-2-methyl-[1,3]dioxane]-5-yloxycarbamoyl}-pentane (Ig)

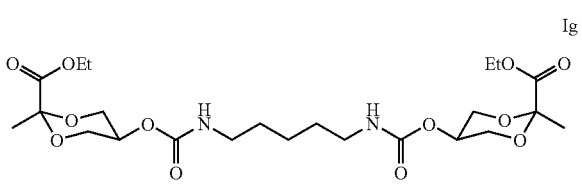

A solution of (Z)-2-ethoxycarbonyl-2-methyl-5-(p-nitrophenoxycarbonyloxy)-[1,3]dioxane (0.23 g, 1.2 mmol) in DCM (2.5 ml) was added to a stirred solution of 1,5-diaminopentane (51 mg, 0.47 mmol) in DCM (0.5 ml) followed by triethylamine (0.25 g, 2.4 mmol). After stirring at room temperature for 1 h the mixture was concentrated, co-evaporated with toluene and chromatographed on silica gel with hexane-acetone (4:1-2:1) to provide the product Ig (253 mg; 100%) as a colorless syrup. $^1$H-NMR (CDCl$_3$): δ 4.79 (tt, 2H, J$_{4e,5}$=J$_{5,6e}$=5.2 Hz, J$_{4a,5}$=J$_{5,6a}$=10.6 Hz, H-5), 4.68-4.64 (m, 2H, NH), 4.28 (q, 4H, J=7.14 Hz, CH$_2$), 4.12 (dd, 4H, J$_{4a,4e}$=J$_{6a,6e}$=11.7 Hz, H-4e, H-6e), 3.56 (dd, 4H, H-4a, H-6a), 3.13-3.09 (m, 4H, NCH$_2$), 1.51 (s, 6H, CH$_3$), 1.30-1.26 (m, 2H, CH$_2$). Electrospray ionization MS m/z: 557 (M+Na$^+$).

Example 10

Bis-1,5-{[(Z)-2-carboxy-2-methyl-[1,3]dioxane]-5-yloxycarbamoyl}-pentane (Ih)

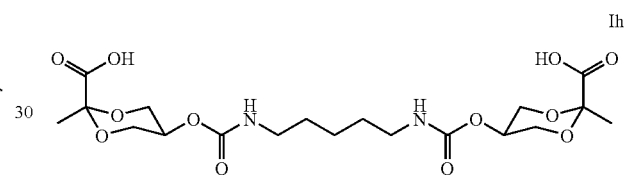

Bis-1,5-{[(Z)-ethoxycarbonyl-2-methyl-[1,3]dioxane]-5-yloxycarbamoyl}-pentane (60 mg, 0.11 mmol) was dissolved in methanol treated with 2 M NaOH (0.25 ml). The solution was stirred at room temperature overnight, then neutralized with Dowex (H$^+$) resin, filtered, concentrated and purified on HPLC reverse-phase (C-8) column. The product was eluted with 100% water to afford the product Ih (37 mg, 72%). $^1$H-NMR (D$_2$O): δ 4.71-4.64 (m, 2H, H-5), 4.14-4.08 (m, 4H, H-4e, H-6e), 3.68-3.62 (m, 4H, H-4a, H-6a), 3.10-3.06 (m, 4H, NCH$_2$), 1.50-1.42 (m, 10H, CH$_2$, CH$_3$), 1.33-1.24 (m, 2H, CH$_2$). Electrospray ionization MS m/z: 545 (M+3Na-2H); 523 (M+2Na—H); 501 (M+Na).

Example 11

Bis-1,6-{[(Z)-2-methoxycarbonyl-2-methyl-[1,3]dioxane]-5-yloxycarbamoyl}-hexane (Ii)

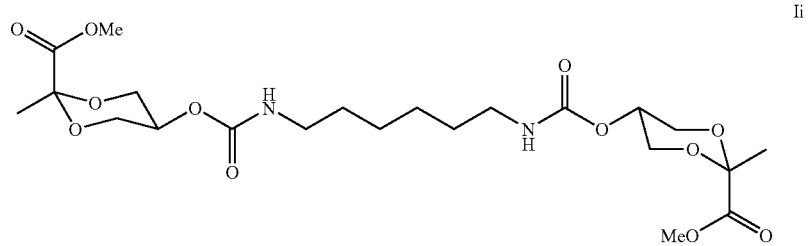

To a solution of 1.6-diaminohexane (57 mg, 0.455 mmol) and (Z)-2-methoxycarbonyl-2-methyl-5-(p-nitrophenoxycarbonyloxy)-[1,3]dioxane (0.23 g, 1.2 mmol) in DCM in the presence of triethylamine (0.25 g, 2.4 mmol). After stirring at room temperature for 1 h the mixture was concentrated, co-evaporated with toluene and chromatographed on silica gel with hexane-acetone (4:1-2:1) to provide title compound Ii (237 mg, 93%). $^1$H-NMR (CDCl$_3$): δ 4.80 (tt, 2H, $J_{4e,5}=J_{5,6e}$=5.22 Hz, H-5), 4.68-4.63 (m, 2H, NH), 4.12 (dd, 4H, $J_{4ea,4e}=J_{6a,6e}$=11.63 Hz, H-4e, H-6e), 3.82 (s, 6H, OCH$_3$), 3.56 (dd, 4H, H-4a, H-6a), 3.14-3.08 (m, 4H, NCH$_2$), 1.54 (s, 3H, CH$_3$), 1.52 (s, 3H, CH$_3$), 1.48-1.40 (m, 4H, CH$_2$), 1.30-1.25 (m, 4H, CH$_2$). Electrospray ionization MS m/z: 543 (M+Na)

Example 12

Bis-1,6-{[(Z)-2-carboxy-2-methyl-[1,3]dioxane]-5-yloxycarbamoyl}-hexane (Ij)

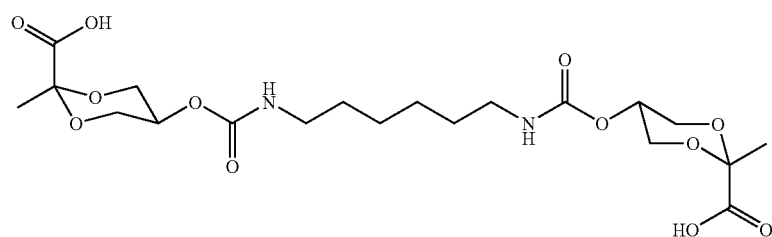

Ij

Bis-1,6-{[(Z)-2-methoxycarbonyl-2-methyl-[1,3]dioxane]-5-yloxycarbamoyl}-hexane (200 mg, 0.38 mmol) was dissolved in methanol and treated with 2 M NaOH (2 ml) overnight. The solution was neutralized with Dowex (H$^+$), filtered and concentrated. Crystallization from MeOH gave (136 mg, 72%) as a white solid Ij. $^1$H-NMR (D$_2$O): δ 4.71-4.63 (m, 2H, H-5), 4.15-4.08 (m, 4H, H-4e, H-6e), 3.68-3.62 (m, 4H, H-4a, H-6a), 3.10-3.06 (m, 4H, NCH$_2$), 1.50-1.40 (m, 12H, CH$_2$, CH$_3$), 1.33-1.24 (m, 2H, CH$_2$). Electrospray ionization MS m/z: 515 (M+Na).

Example 13

Bis-N,N-{[(Z)-2-ethoxycarbonyl-2-methyl-[1,3]dioxane]-5-yloxycarbonyl}-piperazine (Ik)

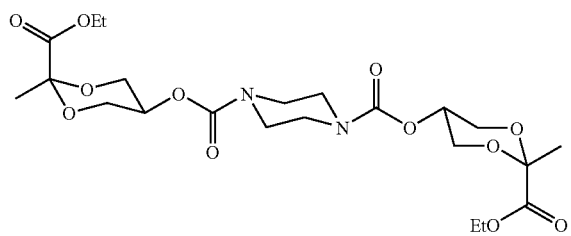

Ik

A solution of (Z)-2-ethoxycarbonyl-2-methyl-5-(p-nitrophenoxycarbonyloxy)-[1,3]dioxane (0.54 g, 1.52 mmol) in DCM (3 ml) was slowly added to a stirred solution of piperazine (52 mg, 0.6 mmol) in DCM (1 ml) followed by triethylamine (0.3 g). The mixture was stirred at room temperature for 1 h, then concentrated co-evaporated with toluene and chromatographed on silica gel with hexane-acetone (4:1-3:1). The product was rectified on silica gel column with hexane-ethyl acetate (4:1-2:1) to provide an oily product Ik (273 mg; 88%). $^1$H NMR (CDCl$_3$): δ 4.84 (tt, 2H, $J_{4e,5}=J_{5,6e}$=5.25, $J_{4a,5}=J_{5,6a}$=9.4 Hz, H-5), 4.29 (q, 4H, J=7.1 Hz, CH$_2$), 4.14 (dd, 4H, H-4e, H-6e), 3.60 (dd, 4H, H-4a, H-6a), 3.38 (bs, 8H, NCH$_2$), 1.52 (s, 6H, CH$_3$), 1.32 (t, 6H, CH$_3$). Electrospray ionization MS m/z: 541 (M+Na).

Example 14

Bis-N,N-{[(Z)-2-carboxy-2-methyl-[1,3]dioxane]-5-yloxycarbonyl}-piperazine (II)

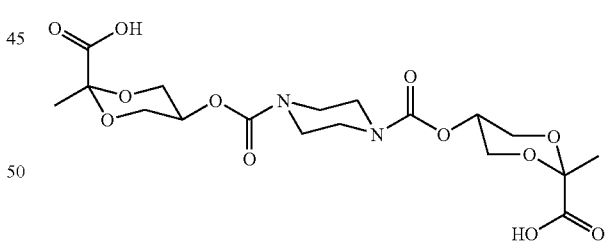

II

Bis-N,N-{[(Z)-2-ethoxycarbonyl-2-methyl-[1,3]dioxane]-5-yloxycarbonyl}-piperazine (82 mg, 0.16 mmol) was dissolved in methanol (2 ml) with a few drops of DCM and 2 M aqueous solution of NaOH (0.25 ml) was added. After 4 h at room temperature the mixture was neutralized with Dowex H$^+$ resin, filtered and concentrated. The product was applied on HPLC (C-18) column and eluted with 100% water, then lyophilized to provide title compound II as a white foam (67 mg, 92%). $^1$H-NMR (D$_2$O): δ 4.74-4.70 (m, 2H, H-5), 4.10 (dd, 4H, $J_{4a,5}=J_{5,6a}$=4.95 Hz, $J_{4a,4e}=J_{6a,6e}$=11.7 Hz, H-4e, H-6e), 3.68 (dd, 4H, $J_{4a,5}=J_{5,6a}$=10.4 Hz, H-4a, H-6a), 3.44 (broad s, 8H, CH$_2$N), 1.45 (s, 6H, CH$_3$). Electrospray ionization MS m/z: 485 (M+Na).

Example 15

N,N-di-[(N-tert-butyloxycarbonyl)-L-alanyno]-piperazine (5)

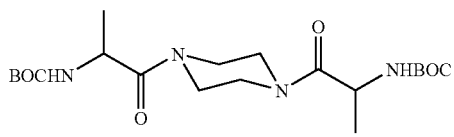

N-tert-Butyloxycarbonyl-L-alanine N-hydroxysuccinimide ester (431 mg, 1.48 mmol) was added to a stirred solution of piperazine (51 mg, 0.59 mmol) in DCM (4 ml) followed by 4-ethyl-morpholine (173 mg, 1.5 mmol). The mixture was stirred at room temperature for 1.5 h then concentrated and chromatographed on silica gel with toluene-acetone (3:1-2:1) to provide product 5 as a white foam (239 mg, 95%). 1H-NMR(CDCl3): δ 5.4 (d, 2H, JCH, NH 8.1 Hz, NH), 4.62 (dt, 2H, J 7.0 Hz, CH), 4.0-3.6 (m, 8H, NCH2), 1.44 (s, 18H, t-Bu), 1.31 (d, 6H, CH3). Electrospray ionization MS m/z: 451 (M+Na).

Example 16

Bis-N,N-{[(Z)-2-ethoxycarbonyl-2-methyl-[1,3]dioxane]-yloxycarbonyl-L-alanylo}-piperazine (Im)

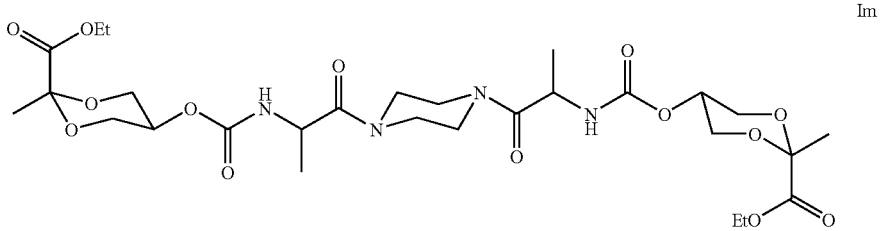

N,N-di-[(N-tert-butyloxycarbonyl)-L-alanyno]-piperazine (110 mg, 0.26 mmol) was dissolved in trifluoroacetic acid (1 ml) and left at room temperature for 1.5 h. The mixture was concentrated; the solid residue was dissolved in methanol (2 ml) and neutralized with 4-ethyl-morpholine, then a solution of (Z)-2-ethoxycarbonyl-2-methyl-5-(p-nitrophenoxycarbonyloxy)-[1,3]dioxane (212 mg, 0.65 mmol) in DCM (1 ml) was added followed by 4-ethyl-morpholine (150 mg, 1.3 mmol) and a few crystals of DMAP. The mixture was stirred at room temperature overnight, then it was concentrated, co-evaporated with toluene and chromatographed on silica gel with hexane-acetone (4:1-2:3) to provide title compound Im as a colorless syrup (114 mg, 67%). $^1$H-NMR (CDCl$_3$): δ 5.68-5.60 (m, 2H, NH), 4.80 (ft, 2H, $J_{4e,5}=J_{5,6e}$=5.3 Hz, $J_{4a,5}=J_{5,6a}$=9.8 Hz, H-5), 4.58 (dq, 2H, JCH, NH 7.3 Hz, J 5.3 Hz, CH), 4.3 (q, 4H, J 7.1, CH$_2$), 4.1 (tt, 4H, $J_{4a,4e}=J_{6a,6e}$=10.9 Hz, H-4e, H-6e), 3.92-3.28 (m, 12H, CH$_2$N, H-4a, H-6a), 1.50 (s, 6H, CH$_3$), 1.33 (t, 6H, CH$_3$), 1.30 (d, 6H, CH$_3$). Electrospray ionization MS m/z: 683 (M+Na).

Example 17

Bis-N,N-{[(Z)-2-carboxy-2-methyl-[1,3]dioxane)-5-yloxycarbonyl-L-alanylo]-piperazine (In)

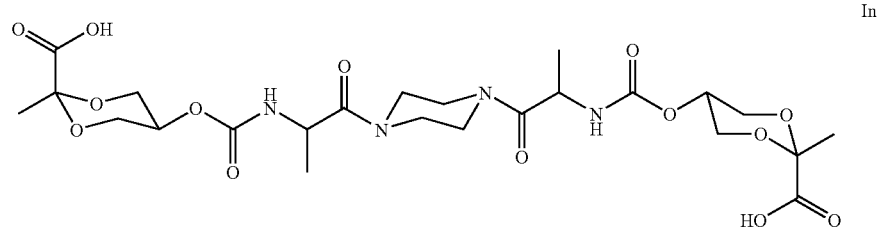

Bis-N,N-{[(Z)-2-ethoxycarbonyl-2-methyl-[1,3]dioxane]-5-yloxycarbonyl-L-alanylo}-piperazine (104 mg, 0.157 mmol) was dissolved in methanol (1.5 ml) and 2 M aqueous NaOH (0.16 ml) was added. After 1.5 h at room temperature the solution was concentrated and dissolved in water (1.5 ml). After 2 h it was neutralized with $CO_2$ and lyophilized to provide title compound In as foam (95 mg). $^1$H-NMR ($D_2O$): δ 4.73-4.66 (m, 2H, H-5), 4.66-4.60 (m, 2H, CH), 4.16-4.04 (m, 4H, H-4e, H-6e), 3.86-3.46 (m, 12H, $CH_2N$, H-4a, H-6a), 1.46 (s, 6H, $CH_3$), 1.36-1.26 (m, 6H, $CH_3$). Electrospray ionization MS m/z: 627 (M+Na).

Example 18

Bis-1,3-[((Z)-2-ethoxycarbonyl-2-methyl-[1,3]dioxane)-5-yloxycarbonyl]-propan-2-ol (Io)

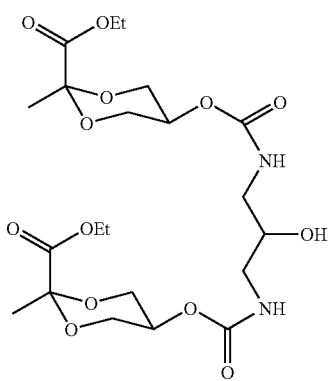

Io

To a solution of (Z)-2-ethoxycarbonyl-2-methyl-5-(p-nitrophenoxycarbonyloxy)-[1,3]dioxane (4.9 g, 13.8 mmol) in DCM (10 mL) a solution of 1,3-diamino-2-hydroxy-propane (518 mg, 5.7 mmol) and $Et_3N$ (3 eq., 4.2 g) was added. After 1 h the mixture was concentrated, and the residue was chromatographed on silica gel with hexane-acetone (70:30-50:50) to give compound Io (2.23 g, 74%).

Example 19

Bis-1,3-{[(Z)-2-ethoxycarbonyl-2-methyl-[1,3]dioxane)-5-yloxycarbamoyl]-2-O-(2,3,4,6-tetra-O-acetylo-b-D-glucopyranozylo)-propan-2ol (Ip)

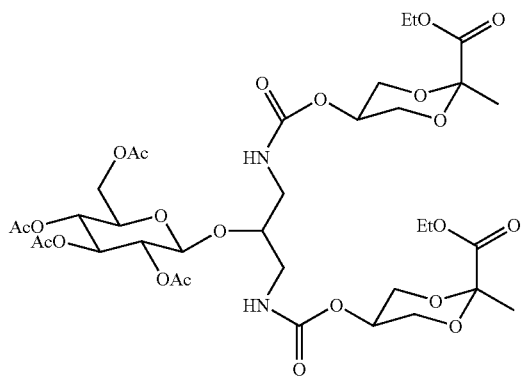

Ip 2,3,4,6-Tetra-O-acetyl-a-D-glucopyranosyl trichloroacetimidate (0.82 g, 1.665 mmol) and Bis-1,3-[((Z)-2-ethoxycarbonyl-2-methyl-[1,3]dioxane)-5-yloxycarbonyl]-propan-2-ol (0.87 g, 1.665 mmol) were dissolved in dry DCM (5 ml) and powdered molecular sieves 4 Å (0.5 g) were added. The mixture was stirred under argon for 1 h, then trimethylsilyl triflate (0.015 ml) was added and the stirring was continued for 1 h. Then the mixture was neutralized with saturated aqueous $NaHCO_3$, filtered through celite and concentrated. The oily residue was chromatographed on silica gel using toluene-ethyl acetate (3:1-1:1) to provide pure compound Ip as a colorless syrup (0.46 g; 32.5%).

Example 20

Bis-1,3-{[(Z)-2-carboxy-2-methyl-1,3-dioxane)-5-yloxycarbamoyl]-2-O-(β-D-glucopyranozylo)-propan-2-ol (Iq)

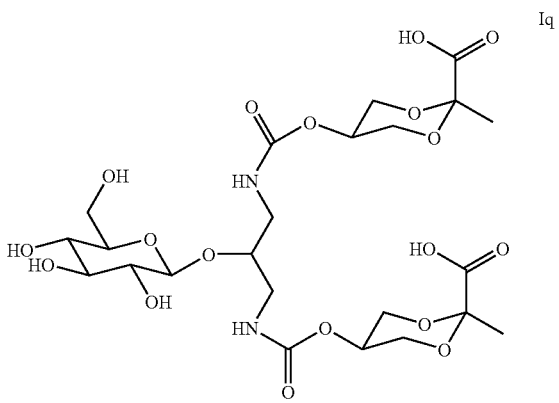

Iq

Obtained from Ip by base hydrolysis.

Example 21

(Z)-2-dimethylaminocarbonyl-5-hydroxy-2-methyl-[1,3]dioxane (6)

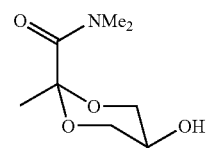

6

4-Methyl-3-oxo-2,5,7-tri-oxa-bicyclo[2.2.2]octane (10 g, 69 mmol) was dissolved in dimethylamine solution (40% wt. in water, 20 ml) with gentle heating (~50-60° C.). After 10 min the mixture was concentrated, co-evaporated with toluene and crystallized from ethyl acetate-hexane to give the title product 6 (10.66 g, 81.7%). $^1$H-NMR ($CDCl_3$): δ 4.01 (ddd, 2H, J 1.3 Hz, J 5.1 Hz, J 11.5 Hz, H-4e, H-6e), 3.89 (ddd, 1H, H-5), 3.49 (dt, 2H, J 1.1 Hz, J 9.7 Hz, H-4a, H-6a), 3.21 (s, 3H, $CH_3$), 2.99 (s, 3H, $CH_3$) 1.49 (s, 3H, $CH_3$). Electrospray ionization MS m/z: 212.1 (M+Na).

Example 22

Bis-1,4-[((Z)-2-dimethylaminocarbonyl-2-methyl-[1,3]dioxane)-5-yloxymethyl]-benzene (7)

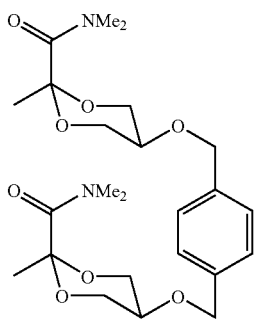

To a suspension of (Z)-2-dimethylaminocarbonyl-5-hydroxy-2-methyl-[1,3]dioxane 6 (1 g, 5.28 mmol) and NaH (60%, 274 mg) in DMF (4 ml) a,a-dibromo-p-xylene (600 mg, 2.27 mmol) was added. The mixture was stirred overnight, MeOH was added followed by brine. Extraction with ethyl acetate and chromatography on silica gel with hexane-acetone (1:1) gave crystalline product 7 (894 mg, 82%). $^1$H-NMR (CDCl$_3$): δ 7.24 (s, 4H, arom.), 4.50 (s, 4H, CH$_2$), 4.04-4.00 (m 4H, H-4e, H-6e), 3.70-3.63 (m, 2H, H-5), 3.59-3.54 (m, 4H, H-4a, H-6a), 3.19 (s, 6H, CH$_3$), 2.99 (s, 6H, CH$_3$) 1.49 (s, 6H, CH$_3$) Electrospray ionization MS m/z: 503.3 (M+Na).

Example 23

Bis-1,4-[((Z)-2-carboxy-2-methyl-[1,3]dioxane)-5-yloxymethyl]-benzene (Ir)

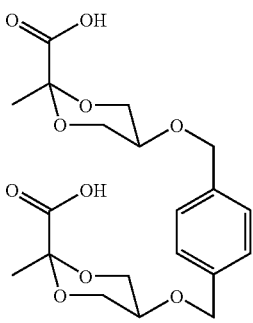

Two solutions one containing bis-1,4-[((Z)-2-dimethylaminocarbonyl-2-methyl-[1,3]dioxane)-5-yloxymethyl]-benzene 7 (250 mg, 0.52 mmol) in MeOH (5 ml) and another containing Na$_2$O$_2$ (121 mg, 3 eq.) in water (5 ml) were combined and the mixture was stirred at 70° C. for two days. The mixture was neutralized by 1N HCl to pH 8 filtered, chromatographed on C-18 column in water and lyophilized to give the compound Ir 165 mg (74%). $^1$H-NMR (D$_2$O): δ 7.48 (s, 4H, arom.), 4.71 (s, 4H, CH$_2$), 4.15 (m, 4H, H-4e, H-6e), 3.90-3.82 (m, 2H, H-5), 3.64-3.59 (m, 4H, H-4a, H-6a), 1.48 (s, 6H, CH$_3$). Electrospray ionization MS m/z: 449.2 (M+Na).

Example 24

Bis-1,3-[((Z)-2-dimethylaminocarbonyl-2-methyl-[1,3]dioxane)-5-yloxymethyl]-benzene (8)

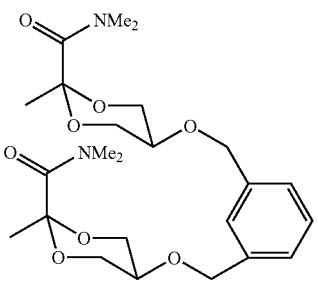

To a suspension of (Z)-2-dimethylaminocarbonyl-5-hydroxy-2-methyl-[1,3]dioxane (1 g, 5.28 mmol) and NaH (60%, 274 mg) in DMF (4 ml) a,a-dibromo-m-xylene (600 mg, 2.27 mmol) was added. The mixture was stirred 1 h, MeOH was added followed by brine. Extraction with ethyl acetate and chromatography on silica gel with hexane-acetone (1:1) gave oil 8 (792 mg, 72%). $^1$H-NMR (CDCl$_3$): δ 7.33-7.20 (m, 4H, arom.), 4.52 (s, 4H, CH$_2$), 4.08-4.04 (m 4H, H-4e, H-6e), 3.73-3.67 (m, 2H, H-5), 3.62-3.58 (m, 4H, H-4a, H-6a), 3.22 (s, 6H, CH$_3$), 3.01 (s, 6H, CH$_3$) 1.50 (s, 6H, CH$_3$). Electrospray ionization MS m/z: 503.3(M+Na).

Example 25

Bis-1,3-[((Z)-2-carboxy-2-methyl-[1,3]dioxane)-5-yloxymethyl]-benzene (Is)

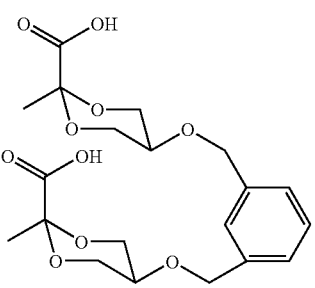

Two solutions one containing bis-1,3-[((Z)-2-dimethylaminocarbonyl-2-methyl-[1,3]dioxane)-5-yloxymethyl]-benzene (250 mg, 0.52 mmol) in MeOH (5 ml) and another containing Na$_2$O$_2$ (121 mg, 3 eq.) in water (5 ml) were combined and the mixture was stirred at 70° C. for two days. The mixture was neutralized by 1N HCl to pH 8 filtered and chromatographed on C-18 (100% water) and lyophilized to give the title compound Is (160 mg, 72%). $^1$H-NMR (D$_2$O): δ 7.48-7.35 (m, 4H, arom.), 4.63 (s, 4H, CH$_2$), 4.15-4.04 (m, 4H, H-4e, H-6e), 3.83-3.73 (m, 2H, H-5), 3.58-3.50 (m, 4H, H-4a, H-6a), 1.41 (s, 6H, CH$_3$). Electrospray ionization MS m/z: 449.2 (M+Na).

Example 26

Bis-1,2-[((Z)-2-dimethylaminocarbonyl-2-methyl-[1,3]dioxane)-5-yloxymethyl]-benzene (9)

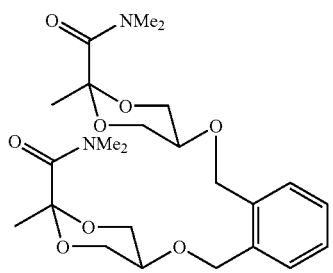

9

To a solution of (Z)-2-dimethylaminocarbonyl-5-hydroxy-2-methyl-[1,3]dioxane (1.088 g 5.75 mmol) and a,a-dibromo-o-xylene (607 mg, 2.3 mmol) in DMF (4 ml) NaH (60%, 276 mg, 6.9 mmol) was added. The mixture was stirred 1.5 h, then MeOH was added followed by brine. Extraction with ethyl acetate and chromatography on silica gel with hexane-acetone (2:1-3:2) gave product contaminated with starting compound. Crystallization from ethanol gave pure title compound 9 (243 mg, 22%). $^1$H-NMR (CDCl$_3$): δ 7.33-7.25 (m, 4H, arom.), 4.60 (s, 4H, CH$_2$), 4.08-4.00 (m 4H, H-4e, H-6e), 3.72-3.52 (m, 6H, H-5, H-4a, H-6a), 3.22 (s, 6H, CH$_3$), 3.01 (s, 6H, CH$_3$) 1.50 (s, 6H, CH$_3$) Electrospray ionization MS m/z: 503.3 (M+Na).

Example 27

Bis-1,2-[((Z)-2-carboxy-2-methyl-[1,3]dioxane)-5-yloxymethyl]-benzene (It)

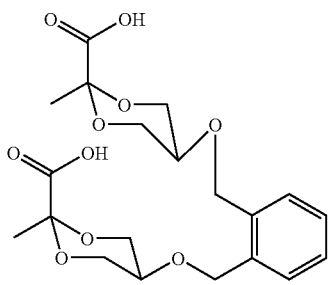

It

Two solutions one containing bis-1,2-[((Z)-2-dimethylaminocarbonyl-2-methyl-[1,3]dioxane)-5-yloxymethyl]-benzene (235 mg, 0.484 mmol) in ethanol (5 ml) and another containing Na$_2$O$_2$ (3 eq.) in water (5 ml) were combined and the mixture was stirred at 80° C. for two days. The mixture was neutralized by 1N HCl to pH 8, filtered, chromatographed on C-18 column with 100% water and lyophilized to give the title compound It (70 mg, 34%). $^1$H-NMR (D$_2$O): δ 7.43-7.40 (m, 4H, arom.), 4.69 (s, 4H, CH$_2$), 4.13-4.08 (m, 4H, H-4e, H-6e), 3.82-3.76 (m, 2H, H-5), 3.56-3.52 (m, 4H, H-4a, H-6a), 1.41 (s, 6H, CH$_3$). Electrospray ionization MS m/z: 449.2 (M+Na).

Example 28

Bis-1,4-[((Z)-2-dimethylaminocarbonyl-2-methyl-[1,3]dioxane)-5-yloxy]-but-2-ene (10)

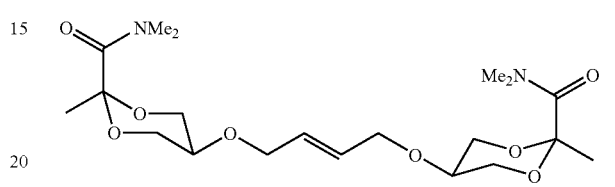

10

To a solution of (Z)-2-dimethylaminocarbonyl-5-hydroxy-2-methyl-[1,3]dioxane (1.08 g 5.7 mmol) and 1,4-dibromobut-2-ene (488 mg, 2.28 mmol) in DMF (4 ml) NaH (60%, 276 mg, 6.9 mmol) was added. The mixture was stirred 1 h, then MeOH was added followed by brine. Extraction with ethyl acetate and chromatography on silica gel with hexane-acetone (2:1) gave the title compound 10 (179 mg, 18%). $^1$H-NMR (CDCl$_3$): δ 5.73-5.70 (m, 2H, CH), 4.10-4.00 (m 8H, H-4e, H-6e, CH$_2$), 3.70-3.50 (m, 6H, H-5, H-4a, H-6a), 3.22 (s, 6H, CH$_3$), 3.01 (s, 6H, CH$_3$) 1.50 (s, 6H, CH$_3$) Electrospray ionization MS m/z: 453.3 (M+Na).

Example 29

Bis-1,4-[((Z)-2-carboxy-2-methyl-1,3-dioxane)-5-yloxymethyl]-but-2-ene (Iu)

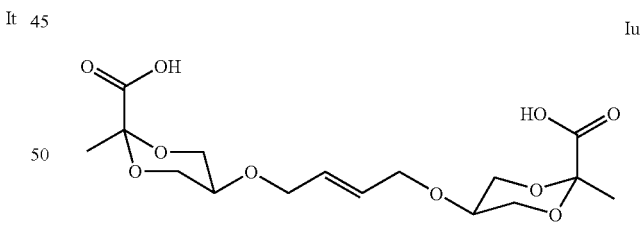

Iu

Two solutions one containing bis-1,4-[((Z)-2-dimethylaminocarbonyl-2-methyl-1,3-dioxane)-5-yloxy]-but-2-ene (25 mg, 0.058 mmol) in ethanol (1 ml) and another containing 2N NaOH (3 eq.) in water (1 ml) were combined and the mixture was stirred at 80° C. for 5 days. The mixture was neutralized by 1 N HCl to pH 8 filtered and chromatographed on C-18 (100% water) and lyophilized to give the title compound Iu (19 mg, 87%). $^1$H-NMR (D$_2$O): δ 5.85-5.82 (m, 2H, CH), 4.13-4.08 (m, 8H, H-4e, H-6e, CH$_2$), 3.74-3.69 (m, 2H, H-5), 3.53-3.49 (m, 4H, H-4a, H-6a), 1.41 (s, 6H, CH$_3$). Electrospray ionization MS m/z: 399.2 (M+Na).

Example 30

Bis-1,6-[((Z)-2-dimethylaminocarbonyl-2-methyl-[1,3]dioxane)-5-yloxy]-hexane (11)

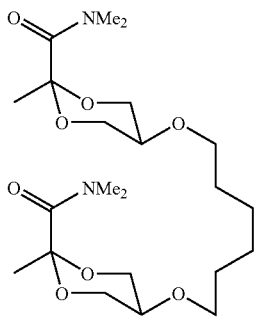

To a suspension of (Z)-2-dimethylaminocarbonyl-5-hydroxy-2-methyl-[1,3]dioxane (1 g 5.28 mmol) and 274 mg NaH (60%) in DMF (4 ml) 1,6-dibromohexane (600 mg, 2.46 mmol) was added followed by $Bu_4NI$ (20 mg). The mixture was stirred 2 h at 80° C. (TLC mobility is only slightly higher then starting amid), MeOH was added followed by brine. Extraction with ethyl acetate and chromatography on silica gel with hexane-acetone (1:1) gave crystalline product 11 (327 mg, 21%). $^1$H-NMR ($CDCl_3$): δ 4.05-4.02 (m 4H, H-4e, H-6e), 3.57-3.47 (m, 6H, H-5, $CH_2O$), 3.43-3.41 (m, 4H, H-4a, H-6a), 3.20 (s, 6H, $CH_3$), 2.98 (s, 6H, $CH_3$) 1.56-1.22 (m, 14H, $CH_3$, $CH_2$). Electrospray ionization MS m/z: 483.3 (M+Na).

Example 31

Bis-1,6-[((Z)-2-carboxy-2-methyl-[1,3]dioxane)-5-yloxy]-hexane (Iv)

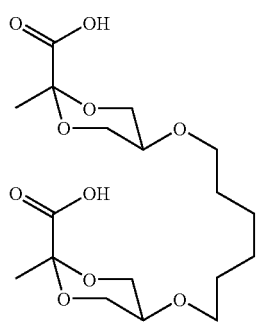

To a solutions of bis-1,6-[((Z)-2-dimethylaminocarbonyl-2-methyl-[1,3]-dioxane)-5-yloxy]-hexane (250 mg, 0.52 mmol) in MeOH (5 ml) and water (1 ml) $Na_2O_2$ (200 mg, eq.) was added and the mixture was stirred at 70° C. for overnight. The mixture was neutralized by 1N HCl to pH 8 filtered and chromatographed on C-18 (100% water) and lyophilized to give the compound Iv (205 mg, 97%). $^1$H-NMR ($D_2O$): δ 4.11-4.08 (m, 4H, H-4e, H-6e), 3.69-3.64 (m, 2H, H-5), 3.61-3.58 (m, 4H, H-4a, H-6a), 1.55-1.50 (m, 4H, $CH_2$), 1.41 (s, 6H, $CH_3$), 1.32-1.29 (m, 4H, $CH_2$). Electrospray ionization MS m/z: 429.2 (M+Na).

Example 32

(Z)-2-Dimethylaminocarbonyl-5-methanesulfonyloxy-2-methyl-[1,3]dioxane (12)

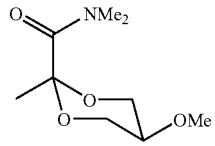

To a solution of (Z)-2-dimethylaminocarbonyl-5-hydroxy-2-methyl-[1,3]dioxane (0.946 g, 5 mmol) in dry DCM (8 ml) dry pyridine (1.2 ml) was added followed by methanesulfonyl chloride (0.8 ml) at 0° C. The temperature was allowed to rise to room temperature and the mixture was stirred for 2.5 h. The mixture was diluted with DCM, washed with brine and concentrated. Chromatography of the residue on silica gel with hexane-acetone (3:1-1:1) gave crystalline product 12 (1.132 g, 85%). $^1$H-NMR ($CDCl_3$): d 4.82-4.76 (m 1H, H-5), 4.21-4.17 (m, 2H, H-4e, H-6e), 3.82-3.78 (m, 2H, H-4a, H-6a), 3.22 (s, 3H, $CH_3$), 3.03 (s, 6H, $CH_3$), 1.55 (s, 3H, $CH_3$). Electrospray ionization MS m/z: 268.1 (M+H).

Example 33

(E)-2-Dimethylaminocarbonyl-5-acetylthio-2-methyl-[1,3]dioxane (13)

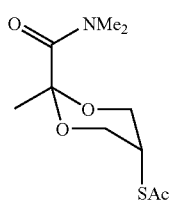

A solution of (Z)-2-Dimethylaminocarbonyl-5-metanesulfonyloxy-2-methyl-[1,3]dioxane 12 (0.905 g, 3.386 mmol) and KSAc (1.329 g, 11.6 mmol) in dry DMF was stirred at 80° C. for 5 h. The mixture was diluted with DCM, filtered through celite and concentrated. Chromatography of the residue on silica gel with hexane-acetone (3:1-2:1) gave the title compound 13 (0.76 g, 80%). $^1$H-NMR ($CDCl_3$): δ 4.30-4.27 (m, 2H, H-4e, H-6e), 3.90-3.87 (m, 2H, H-$4_a$, H-$6_a$), 3.61-3.59 (m 1H, H-5), 3.21 (s, 3H, $CH_3$), 3.03 (s, 6H, $CH_3$), 2.38 (s, 3H, SAc), 1.55 (s, 3H, $CH_3$). Electrospray ionization. MS m/z: 248.1 (M+H).

Example 34

Bis-1,3-[((E)-2-dimethylaminocarbonyl-2-methyl-[1,3]dioxane)-5-ylthio]-2-hydroxy-propane (14)

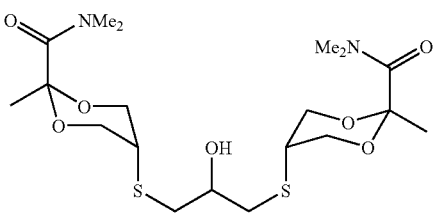

To a solution of (E)-2-Dimethylaminocarbonyl-5-acetylthio-2-methyl-[1,3]dioxane 13 (0.133 g, 0.538 mmol) and epibromohydrine (21 ml, 0.235 mmol) in MeOH (1 ml) $K_2CO_3$ (76 mg, 0.54 mmol) was added under argon. The mixture was stirred for 2 h then diluted with DCM, filtered through celite and concentrated. Chromatography of the residue on silica gel with hexane-acetone (2:1-1:2) gave the title compound 14 (100 mg, 90%). $^1$H-NMR (CDCl$_3$): δ 4.28-4.2 (m 4H, H-4e, H-6e), 4.00-3.95 (m, 4H, H-4a, H-6a), 3.89-3.85 (m, 1H, CHOH), 3.22 (s, 6H, CH$_3$), 3.02 (s, 6H, CH$_3$), 2.91-2.85 (m, 4H, H-5, CH$_2$S), 2.75 (dd, 2H, J 7.5 Hz, J 13.8 Hz, CH$_2$S), 1.58 (s, 6H, CH$_3$) Electrospray ionization MS m/z: 489.1 (M+Na).

Example 35

Bis-1,3-[((E)-2-carboxy-2-methyl-[1,3]dioxane)-5-ylthio]-2-hydroxy-propane (Iw)

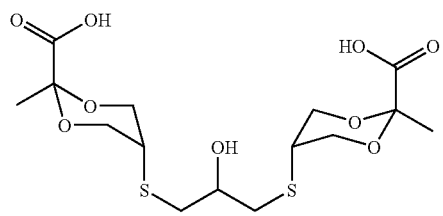

To a solutions of bis-1,4-[((E)-2-dimethylaminocarbonyl-2-methyl-[1,3]dioxane)-5-ylthio]-2-hydroxy-propane 14 (76 mg, 0.163 mmol) in ethanol (2.5 ml) and 2 M NaOH (0.8 ml) was added and the mixture was stirred at 80° C. overnight. The mixture was neutralized with DOWEX (H+-form) to pH 8 filtered and concentrated. The residue was lyophilized to give the title product Iw (65 mg, 97%). $^1$H-NMR (D$_2$O): δ 4.23-4.19 (m, 4H, H-4e, H-6e), 4.00-3.95 (m, 1H, CHOH), 3.94-3.90 (m, 4H, H-4a, H-6a), 2.98-2.96 (m, 2H, H-5), 2.91 (dd, 2H, J 4.6 Hz, J 13.8 Hz, CH$_2$S), 2.79 (dd, 2H, J 7.4 Hz, J 13.8 Hz, CH$_2$S), 1.43 (s, 6H, CH$_3$). Electrospray ionization MS m/z: 435.0 (M+Na).

Example 36

Bis-1,6-[((E)-2-dimethylaminocarbonyl-2-methyl-[1,3]dioxane)-5-ylthio]-hexane (15)

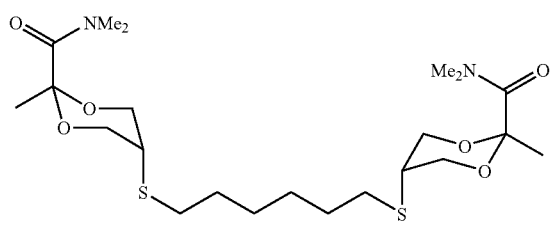

To a solution of (E)-2-Dimethylaminocarbonyl-5-acetylthio-2-methyl-[1,3]dioxane 13 (154 mg, 0.622 mmol) and 1,6-dibromohexane (44 ml, 0.283 mmol) in MeOH (1 ml) K$_2$CO$_3$ (86 mg, 0.622 mmol) was added under argon. The mixture was stirred for 2 h then diluted with DCM, filtered through celite and concentrated. Chromatography of the residue on silica gel with hexane-acetone (2:1-1:1) gave the title compound 15 (127 mg, 91%). $^1$H-NMR (CDCl$_3$): δ 4.22-4.18 (m 4H, H-4e, H-6e), 3.96-3.91 (m, 4H, H-4a, H-6a), 3.23 (s, 6H, CH$_3$), 3.02 (s, 6H, CH$_3$), 2.76-2.73 (m, 2H, H-5), 2.61 (t, 4H, J 7.4 Hz, CH$_2$S), 1.64-1.59 (m, 4H, CH$_2$), 1.60 (s, 6H, CH$_3$), 1.44-1.40 (m, 4H, CH$_2$), Electrospray ionization MS m/z: 515.2 (M+Na).

Example 37

Bis-1,6-[((E)-2-carboxy-2-methyl-[1,3]dioxane)-5-ylthio]-hexane (Ix)

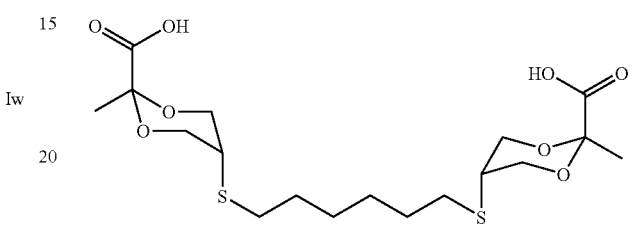

To a solutions of bis-1,6-[((E)-2-dimethylaminocarbonyl-2-methyl-[1,3]dioxane)-5-ylthio]-hexane 15 (99 mg, 0.2 mmol) in ethanol (2.5 ml) and 2M NaOH (1 ml) was added and the mixture was stirred at 80° C. overnight. The mixture was neutralized with DOWEX (H+-form) to pH 8 filtered and concentrated. The residue was lyophilized to give the title product Ix (80 mg, 96%). $^1$H-NMR (D$_2$O): δ 4.21-4.18 (m, 4H, H-4e, H-6e), 3.90-3.87 (m, 4H, H-4a, H-6a), 2.92-2.90 (m, 2H, H-5), 2.66-2.63 (t, 4H, J 7.4 Hz, CH$_2$S), 1.64-1.60 (m, 4H, CH$_2$S), 1.43-1.40 (m, 10H, CH$_3$, CH$_2$S). Electrospray ionization MS m/z: 461.1 (M+Na).

Example 38

Bis-1,4-[((E)-2-dimethylaminocarbonyl-2-methyl-[1,3]dioxane)-5-ylthio]-but-2-ene (16)

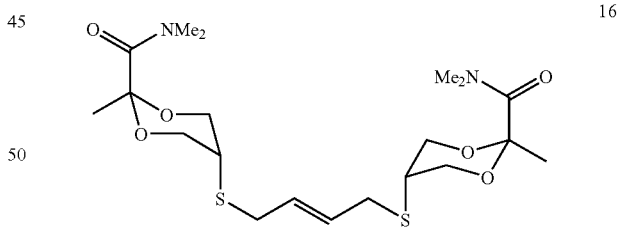

To a solution of (E)-2-dimethylaminocarbonyl-5-acetylthio-2-methyl-[1,3]dioxane 13 (149 mg, 0.6 mmol) and 1,4dibromo-but-2-ene (59 mg, 0.27 mmol) in MeOH (1.5 ml) K$_2$CO$_3$ (83 mg, 0.6 mmol) was added under argon. The mixture was stirred overnight then diluted with DCM, filtered through celite and concentrated. Chromatography of the residue on silica gel with hexane-acetone (3:1-1:1) gave the title compound 16 (105 mg, 85%). $^1$H-NMR (CDCl$_3$): δ 5.58-5.56 (m, 2H, CH), 4.22-4.18 (m 4H, H-4e, H-6e), 3.92-3.90 (m, 4H, H-4a, H-6a), 3.24-3.20 (m, 10H, CH$_2$, CH$_3$), 3.02 (s, 6H, CH$_3$), 2.70-2.68 (m, 2H, H-5), 1.59 (s, 6H, CH$_3$). Electrospray ionization MS m/z: 485.1 (M+Na).

Example 39

Bis-1,4-[((E)-2-carboxy-2-methyl-[1,3]dioxane)-5-ylthio]-but-2-ene (Iy)

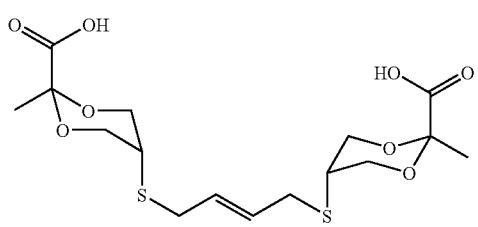

To a solutions of bis-1,4-[((E)-2-dimethylaminocarbonyl-2-methyl-[1,3]dioxane)-5-ylthio]-but-2-ene 16 (81 mg, 0.175 mmol) in ethanol (2 ml) and 2M NaOH (0.9 ml) was added and the mixture was stirred at 80° C. for 2 days. The mixture was neutralized with DOWEX (H+-form) to pH 8 filtered and concentrated. The residue was lyophilized to give the title product 1y dimethylammonium salt (85 mg). $^1$H-NMR (D$_2$O): δ 5.67-5.65 (m, 2H, CH), 4.21-4.19 (m, 4H, H-4e, H-6e), 3.89-3.86 (m, 4H, H-4a, H-6a), 3.27-3.26 (m, 4H, CH$_2$), 2.86-2.84 (m, 2H, H-5), 1.42 (s, 6H, CH$_3$). Electrospray ionization MS m/z: 458.1 (M+Na).

Example 40

Bis-1,4-[((E)-2-dimethylaminocarbonyl-2-methyl-[1,3]dioxane)-5-thiomethyl]-benzene (17)

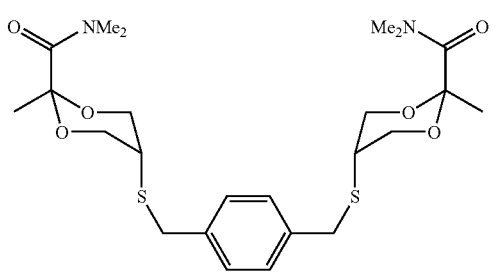

To a solution of (E)-2-dimethylaminocarbonyl-5-acetylthio-2-methyl-[1,3]dioxane 13 (142 mg, 0.574 mmol) and a,a-dibromo-p-xylene (71 mg, 0.26 mmol) in MeOH (1.5 ml) K$_2$CO$_3$ (80 mg, 0.574 mmol) was added under argon. The mixture was stirred for 5 h then diluted with DCM, filtered through celite and concentrated. Chromatography of the residue on silica gel with hexane-acetone (2:1-1:1) gave the title compound 17 (108 mg, 81%). $^1$H-NMR (CDCl$_3$): δ 7.26 (s, 4H, arom.), 4.12-4.10 (m 4H, H-4e, H-6e), 3.86-3.83 (m, 4H, H-4a, H-6a), 3.80 (s, 4H, CH$_2$), 3.20 (s, 6H, CH$_3$), 3.00 (s, 6H, CH$_3$), 2.61-2.59 (m, 2H, H-5), 1.51 (s, 6H, CH$_3$). Electrospray ionization MS m/z: 535.1 (M+Na).

Example 41

Bis-1,4-[((E)-2-carboxy-2-methyl-[1,3]dioxane)-5-thiomethyl]-benzene (Iz)

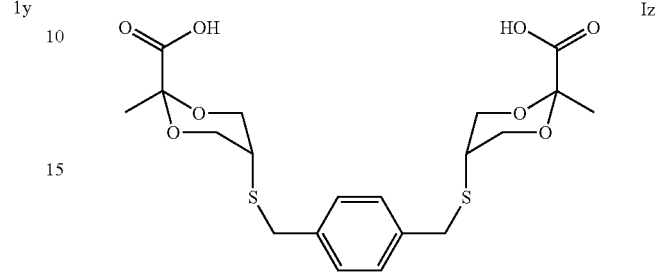

To a solutions of bis-1,4-[((E)-2-dimethylaminocarbonyl-2-methyl-[1,3]-dioxane)-5-thiomethyl]-benzene 17 (88 mg, 0.17 mmol) in ethanol (2.5 ml) and 2M NaOH (0.85 ml) was added and the mixture was stirred at 80° C. overnight. The mixture was neutralized with DOWEX (H+-form) to pH 8 filtered and concentrated. The residue was lyophilized to give the title product Iz sodium salt (85 mg). $^1$H-NMR (D$_2$O): δ 7.35 (s, 4H, arom.), 4.15-4.10 (m, 4H, H-4e, H-6e), 3.85 (s, 4H, CH$_2$), 3.80-3.77 (m, 4H, H-4a, H-6a), 2.78-2.75 (m, 2H, H-5), 1.42 (s, 6H, CH$_3$). Electrospray ionization MS m/z: 481.0 (M+Na).

Example 42

(Z)-5-allyloxy-2-dimethylaminocarbonyl-2-methyl-[1,3]dioxane (18)

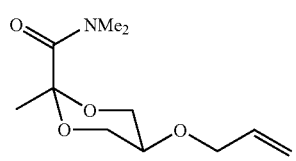

To a solution of (Z)-2-dimethylaminocarbonyl-5-hydroxy-2-methyl-[1,3]dioxane (5 g, 26.4 mmol) in dry DMF (18 ml) NaH (60%, 1.75 g) was added. Allyl bromide (3.5 ml, 39 mmol) was slowly added to the suspension. The mixture was stirred for 1 h at room temperature then MeOH (2 ml) was added followed by brine and the mixture was extracted with ethyl acetate. Organic fraction was collected and concentrated. Chromatography of the residue on silica gel with hexane-acetone (4:1-3:1) gave the title compound 18 (5.5 g, 91%). $^1$H-NMR (CDCl$_3$): δ 5.91-5.78 (m, 1H, CH), 5.30-5.16 (m, 2H, CH$_2$), 4.10-4.00 (m, 4H, CH$_2$, H-4e, H-6e), 3.70-3.52 (m, 3H, H-5, H-4a, H-6a), 3.21 (s, 3H, CH$_3$), 3.00 (s, 3H, CH$_3$), 1.50 (s, 3H, CH$_3$). Electrospray ionization MS m/z: 230.2 (M+H).

Example 43

(Z)-2-dimethylaminocarbonyl-5-glycidyloxy-2-methyl-[1,3]dioxane (19)

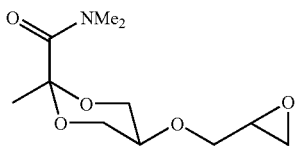

A mixture of (Z)-5-allyloxy-2-dimethylaminocarbonyl-2-methyl-[1,3]dioxane 18 (5.05 g, 22 mmol) and 3-chloro-peroxybenzoic acid (6 g, 35 mmol) in CHCl$_3$ (30 ml) was stirred at 60° C. for 2 h then more mCPBA (1.35 g, 7.5 mmol) was added and the stirring continued for 1 h. The mixture was diluted with DCM, washed with aq. NaHCO$_3$ and organic fraction was concentrated. Chromatography of the residue on silica gel in hexane-acetone (3:1-3:2) gave the title compound 19 (4.46 g, 83%). $^1$H-NMR (CDCl$_3$): δ 4.10-4.04 (m, 2H, H-4e, H-6e), 3.76 (dd, 1H, J 2.8 Hz, J 11.5 Hz, CH$_2$), 3.66-3.60 (m, 1H, H-5), 3.56-3.53 (m, 2H, H-4a, H-6a), 3.39 (dd, 1H, J 5.8 Hz, J 11.5 Hz, CH$_2$), 3.20 (s, 3H, CH$_3$), 3.06-3.03 (m, 1H, CH), 2.99 (m, 1H, CH), 2.76 (t, 1H, J 4.4 Hz, CH$_2$), 2.56 (dd, 1H, J 2.7 Hz, J 5.0 Hz, CH$_2$), 1.49 (s, 3H, CH$_3$). Electrospray ionization MS m/z: 268.1 (M+Na).

Example 44

2,6-Di-glycidyloxy-1,7-di-[((Z)-2-dimethylaminocarbonyl-2-methyl-[1,3]dioxane)-5-yloxy]-4-thiaheptane (20)

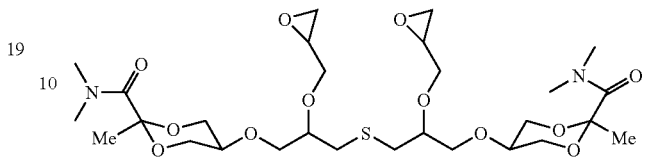

(Z)-2-Dimethylaminocarbonyl-5-glycidyloxy-2-methyl-[1,3]dioxane 19 (2.45 g, 10 mmol) and KSAc (0.51 g, 4.46 mmol) were dissolved in MeOH (5 ml) and refluxed for 10 min. The mixture was stirred for 1 h at room temperature then concentrated, taken up in DCM, washed with brine and concentrated. The residue was dried on oil pump. To a solution of the residue in dry DMF (5 ml) NaH (60%, 600 mg, 15 mmol) and epibromohydrine (15 mmol) were added. After 30 min the reaction was quenched with MeOH, taken up in ethyl acetate, washed with brine and concentrated. Chromatography of the residue on silica gel with hexane-acetone (5:5-6:4) gave the title product 20 (2.29 g, 75%). $^1$H-NMR (CDCl$_3$): δ 4.10-4.05 (m, 4H, H-4e, H-6e), 3.94-3.84 (m, 2H, CH$_2$), 3.72-3.52 (m, 12H, H-4a, H-6a, H-5, CH, CH$_2$), 3.48-3.42 (m, 2H, CH$_2$), 3.22 (s, 6H, CH$_3$), 3.14-3.10 (m, 2H, OCH), 3.02 (s, 6H, CH$_3$), 2.80-2.78 (m, 2H, OCH), 2.72-2.66 (m, 4H, SCH$_2$), 2.61-2.58 (m, OCH), 1.52 (s, 6H, CH$_3$). Electrospray ionization MS m/z: 659.4 (M+Na).

Example 45

4,7,10,13,16,19,22-hepta-oxa-pentacosane-1,24-diene (21)

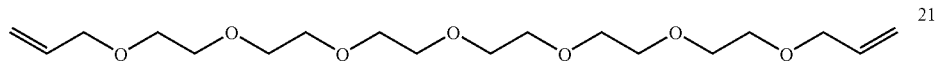

To a solution of hexa(ethylene glycol)(5 g, 17.18 mmol) in DMF (25 ml) NaH (60%, 2.6 g, 65 mmol) was slowly added followed by allyl bromide (4.6 ml, 53 mmol). After 1 h the reaction was quenched with MeOH, diluted with brine and extracted with ethyl acetate. The organic layer was collected, concentrated and the residue was chromatographed on silica gel with hexane-acetone (7:3-2:1) to give a thin syrup of the compound 21 (5.47 g, 85%). $^1$H-NMR (CDCl$_3$): δ 5.95-5.88 (m, 2H, CH), 5.29-5.25 (m, 2H, CH$_2$), 5.19-5.16 (m, 2H, CH$_2$), 4.03-4.01 (m, 4H, CH$_2$), 3.67-3.65 (m, 20H, CH$_2$O), 3.61-3.59 (m, 4H, CH$_2$O).

Example 46

1,25-Di-acetylthio-4,7,10,13,16,19,22-hepta-oxa-pentacosane

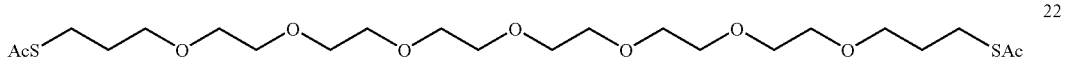

A solution of 4,7,10,13,16,19,22-hepta-oxa-pentacosane-1,24-diene 21 (5.46 g, 15 mmol) and thioacetic acid (4.5 ml, 60 mmol) in DCM (25 ml) was irradiated with UV lamp (254 nm) for 4 h. The mixture was concentrated and chromatographed on silica gel in hexane:acetone 3:1-2:1 to give a thin syrup 22 (7.02 g, 91%). $^1$H-NMR (CDCl$_3$): δ 3.65-3.62 (m, 20H, CH$_2$O, CH$_2$C$\underline{H}_2$O), 3.59-3.57 (m, 4H, CH$_2$C$\underline{H}_2$O), 3.51 (t, 4H, J 6.1 Hz, CH$_2$C$\underline{H}_2$O), 2.95 (t, 4H, J 7.2 Hz, CH$_2$S), 2.32 (s, 6H, SAc), 1.85 (p, 4H, SCH$_2$C$\underline{H}_2$CH$_2$O). Electrospray ionization MS m/z: 537.2 (M+Na).

Example 47

5,9-Di-{[((Z)-2-carboxy-2-methyl-[1,3]dioxane)-5-yloxy]methyl}-2,12-di-hydroxy-1-mercapto-4,10,18,21,24,27,30,33,36-nona-oxa-7,14-di-thia-nonatria-contane (Ia')

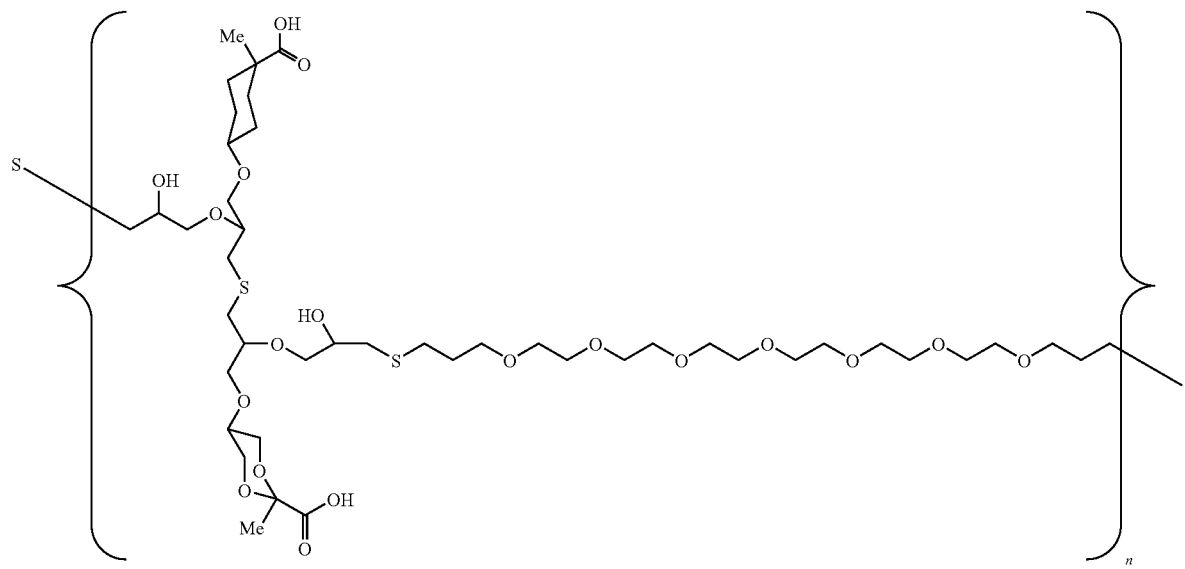

To a solution of 2,6-Di-glycidyloxy-1,7-di-[((Z)-2-dimethylaminocarbonyl-2-methyl-[1,3]dioxane)-5-yloxy]-4-thia-heptane 20 (141 mg, 0.22 mmol) 1,25-di-acetylthio-4,7,10,13,16,19,22-hepta-oxa-pentacosane 22 (107 mg, 0.208 mmol) in MeOH (5 ml) K$_2$CO$_3$ (30 mg) was added. After 5 h NMR of a sample shows no Ac group. The mixture was filtered, concentrated, dissolved in MeOH (5 ml) and NaOH (100 mg) in water (5 mL) was added. The mixture was stirred at 80° C. for 2 days then neutralized with acetic acid, dialyzed via 10K membrane concentrator and freeze dried to give 115 mg of polymeric material Ia'. $^1$H-NMR (D$_2$O): δ 4.14-4.10 (m, 4H, H-4e, H-6e), 3.96-3.92 (m, 2H, C$\underline{H}$OH), 3.82-3.60 (m, 40H, H-5, C$\underline{H}$OH, OCH$_2$), 3.55-3.50 (m, 4H, H-4a, H-6a), 2.81-2.64 (m, 12H, CH$_2$S), 1.92-1.86 (m, 4H, CH$_2$), 1.42 (s, 6H, CH$_3$).

Example 48

1-Acetylthio-3-[((Z)-2-dimethylaminocarbonyl-2-methyl-[1,3]dioxane)-5-yloxy]-propane (23)

A solution of (Z)-5-allyloxy-2-dimethylaminocarbonyl-2-methyl-[1,3]dioxane (5.35 g, 23.33 mmol) and thioacetic acid (3.6 ml, 49 mmol) in DCM (7 ml) was irradiated with UV lamp (254 nm) for 5 h. The mixture was concentrated and the residue was chromatographed on silica gel in hexane-acetone (3:1-2:1) to give the title compound 23 (5.58 g, 78%). $^1$H-NMR (CDCl$_3$): δ 4.08-4.04 (m, 2H, H-4e, H-6e), 3.58-3.50 (m, 5H, H-5, H-4a, H-6a, OCH$_2$), 3.22 (s, 3H, CH$_3$), 3.01 (s, 3H, CH$_3$), 2.90 (t, 2H, CH$_2$S), 2.32 (s, 3H, SAc), 1.82-1.77 (m, 2H, SCH$_2$CH$_2$), 1.52 (s, 3H, CH$_3$). Electrospray ionization MS m/z: 328.1 (M+H).

Example 49

1,11-Di-[((Z)-2-dimethylaminocarbonyl-2-methyl-[1,3]dioxane)-5-yloxy]-6-hydroxy-4,8-di-thia-undecane (24)

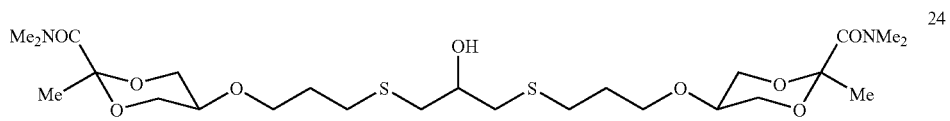

To a solution of 1-acetylthio-3-[((Z)-2-dimethylaminocarbonyl-2-methyl-[1,3]dioxane)-5-yloxy]-propane 23 (1.165 g, 3.81 mmol) in MeOH (4 ml) K$_2$CO$_3$ (526 mg, 3.8 mmol) was added followed by epibromohydrine (150 ml, 1.75 mmol) in 3 portions within 1 h. After 2 h the mixture was diluted with DCM, filtered and concentrated. The residue was redissolved in MeOH, silica gel was added and the solvent was removed in vacuum. The slurry of the residue with DCM was loaded on silica gel column. Chromatography on silica gel with hexane-acetone (3:1-1:1) gave the title compound 24 (0.59 g, 58%). $^1$H-NMR (CDCl$_3$): δ 4.08-4.05 (m, 4H, H-4e, H-6e), 3.81-3.77 (m, 1H, CHOH), 3.61-3.51 (m, 10H, H-5, H-4a, H-6a, OCH$_2$), 3.23 (s, 6H, CH$_3$), 3.01 (s, 6H, CH$_3$), 2.73 (dd, 2H, J 4.6 Hz, J 13.5 Hz, CH$_2$S), 2.63-2.58 (m, 6H, CH$_2$S), 1.80 (p, 4H, J 7.0 Hz, SCH$_2$CH$_2$), 1.52 (s, 6H, CH$_3$). Electrospray ionization MS m/z: 605.2 (M+Na).

Example 50

1,11-Di-[((Z)-2-carboxy-2-methyl-[1,3]dioxane)-5-yloxy]-6-hydroxy-4,8-di-thia-undecane (Ib')

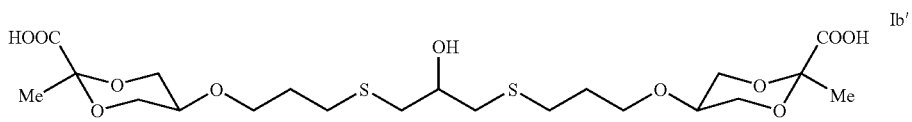

To a solution of 1,11-Di-[((Z)-2-dimethylaminocarbonyl-2-methyl-[1,3]dioxane)-5-yloxy]-6-hydroxy-4,8-di-thia-undecane 24 (124 mg, 0.21 mmol) in ethanol (1.5 ml) 2N NaOH (2.1 ml) was added and the mixture was stirred at 80° C. for 2 days. The mixture was neutralized by DOWEX (H+-form) to pH 8 filtered and lyophilized to give title compound Ib' (96 mg, 87%). $^1$H-NMR (D$_2$O): δ 4.12-4.08 (m, 4H, H-4e, H-6e), 3.95-3.90 (m, 1H, CHOH), 3.71-3.63 (m, 6H, H-5, OCH$_2$), 3.52-3.48 (m, 4H, H-4a, H-6a), 2.81 (dd, 2H, J 4.9 Hz, J 13.7 Hz, CH$_2$S), 2.69 (dd, 2H, J 7.14 Hz, J 13.7 Hz, CH$_2$S), 2.63-2.58 (t, 4H, J 7.2 Hz, CH$_2$S), 1.80 (p, 4H, J 7.2 Hz, SCH$_2$CH$_2$), 1.41 (s, 6H, CH$_3$). Electrospray ionization MS m/z: 551.1 (M+Na).

Example 51

1,11-Di-[((Z)-2-dimethylaminocarbonyl-2-methyl-[1,3]dioxane)-5-yloxy]-6-glycidyloxy-4,8-di-thia-undecane (25)

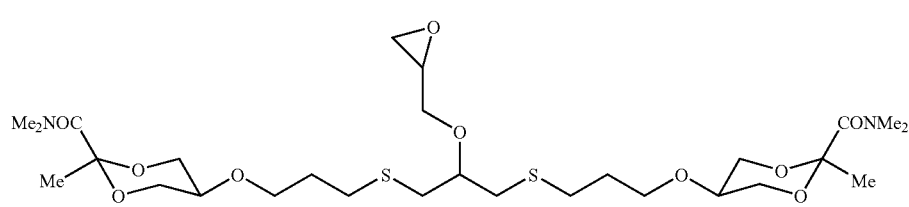

To a solution of 1,11-Di-[((Z)-2-dimethylaminocarbonyl-2-methyl-[1,3]dioxane)-5-yloxy]-6-hydroxy-4,8-di-thia-undecane 24 (3.33 g, 5.72 mmol) in dry DMF (12 ml) NaH (60%, 460 mg) was added followed by epibromohydrine (1 ml, 2 eq). The mixture was stirred at room temperature for 1 h then MeOH (1 ml) and brine was added. Extraction with ethyl acetate followed by chromatography on silica gel in DCM-MeOH (50:1-25:1) gave the title product 25 (2.85 g, 80%). $^1$H-NMR (CDCl$_3$): δ 4.08-4.05 (m, 4H, H-4e, H-6e), 3.88-3.85 (m, 1H, CH), 3.66-3.42 (m, 12H, H-5, H-4a, H-6a, OCH$_2$), 3.22 (s, 6H, CH$_3$), 3.16-3.14 (m, 1H, OCH), 3.02 (s, 6H, CH$_3$), 2.81-2.58 (m, 10H, OCH, CH$_2$S), 1.82-1.77 (m, 4H, SCH$_2$C$\underline{H}_2$), 1.52 (s, 6H, CH$_3$). Electrospray ionization MS m/z: 661.2 (M+Na).

Example 52

1,1,37,37-Tetra-{5-[((Z)-2-dimethylaminocarbonyl-2-methyl-[1,3]dioxane)-5-yloxy]-2-thia-pentyl}-4,34-dihydroxy-2,10,13,16,19,22,25,28,36-nona-oxa-6,32-di-thia-heptatriacontane 26

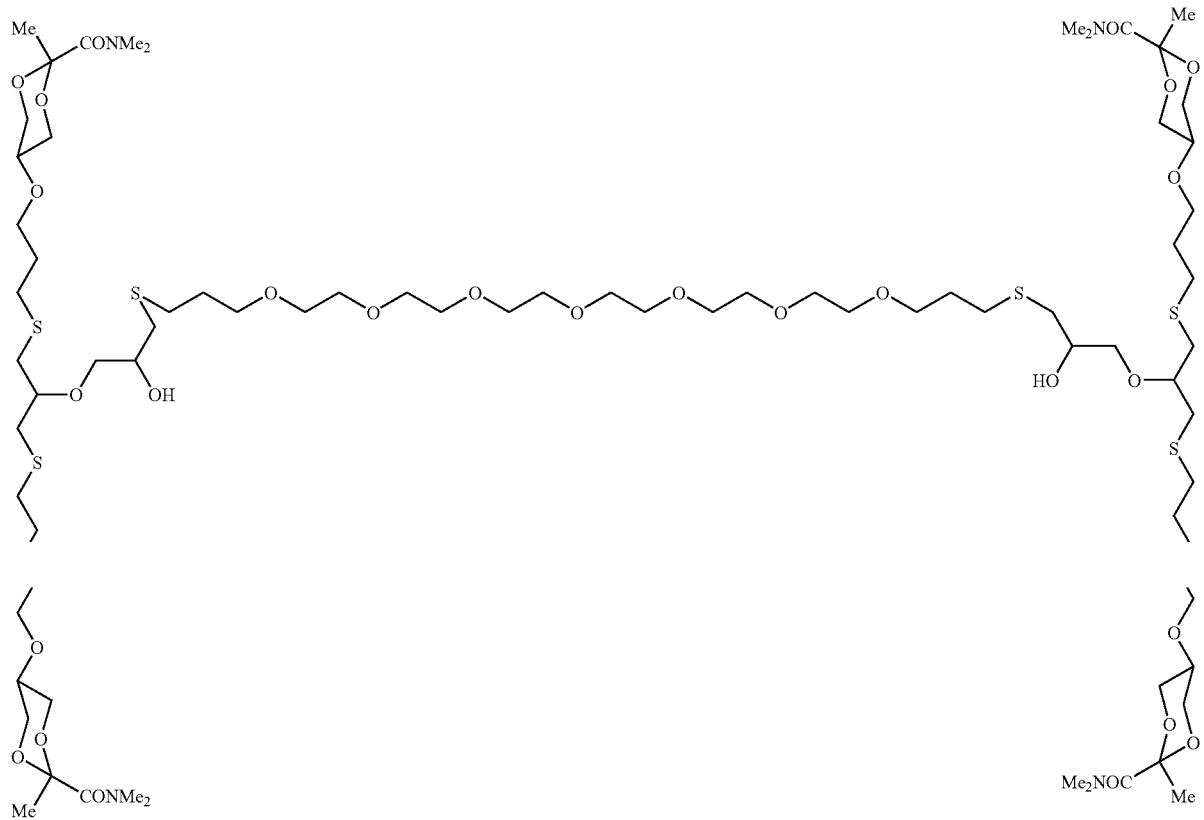

To a solution of 1,11-Di-[((Z)-2-dimethylaminocarbonyl-2-methyl-[1,3]dioxane)-5-yloxy]-6-glycidyloxy-4,8-di-thia-undecane 25 (208 mg, 0.325 mmol) and 1,25-Di-acetylthio-4,7,10,13,16,19,22-hepta-oxa-pentacosane (76 mg, 0.148 mmol) in MeOH (2 ml) $K_2CO_3$ (41 mg, 0.3 mmol) was added. The mixture was stirred overnight at room temperature then diluted with DCM, filtered through celite and concentrated. Chromatography of the residue on silica gel with DCM-MeOH (50:1-20:1) gave the product 26 (205 mg, 81%). $^1$H-NMR (CDCl$_3$): δ 4.08-4.04 (m, 8H, H-4e, H-6e), 3.88-3.85 (m, 2H, CH), 3.68-3.50 (m, 54H, H-5, H-4a, H-6a, OCH, OCH$_2$), 3.23 (s, 12H, CH$_3$), 3.02 (s, 12H, CH$_3$), 2.76-2.57 (m, 24H, CH$_2$S), 1.89-1.77 (m, 12H, SCH$_2$C$\underline{H}_2$), 1.52 (s, 12H, CH$_3$). Electrospray ionization MS m/z: 1729.8 (M+Na).

Example 53

1,1,37,37-Tetra-{5-[((Z)-2-carboxy-2-methyl-[1,3]dioxane)-5-yloxy]-2-thia-pentyl}-4,34-di-hydroxy-2,10,13,16,19,22,25,28,36-nona-oxa-6,32-di-thia-heptatriacontane (Ic')

CH$_2$S), 2.70-2.63 (m, 14H, CH$_2$S), 1.92-1.82 (m, 12H, SCH$_2$C$\underline{H}_2$), 1.42 (s, 12H, CH$_3$). Electrospray ionization MS m/z: 1706.3 (M+Na).

Example 54

3,6,9,12,15,18-hexa-oxa-undecosan-20-eneol (27)

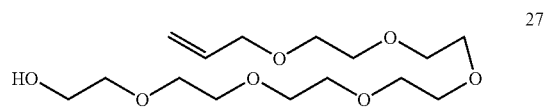

To a solution of hexa(ethylene glycol)(10.16 g, 35.98 mmol) in DMF (28 ml) NaH (60%, 2.24 g, 56 mmol) was slowly added followed by allyl bromide (3.2 ml, 35.57

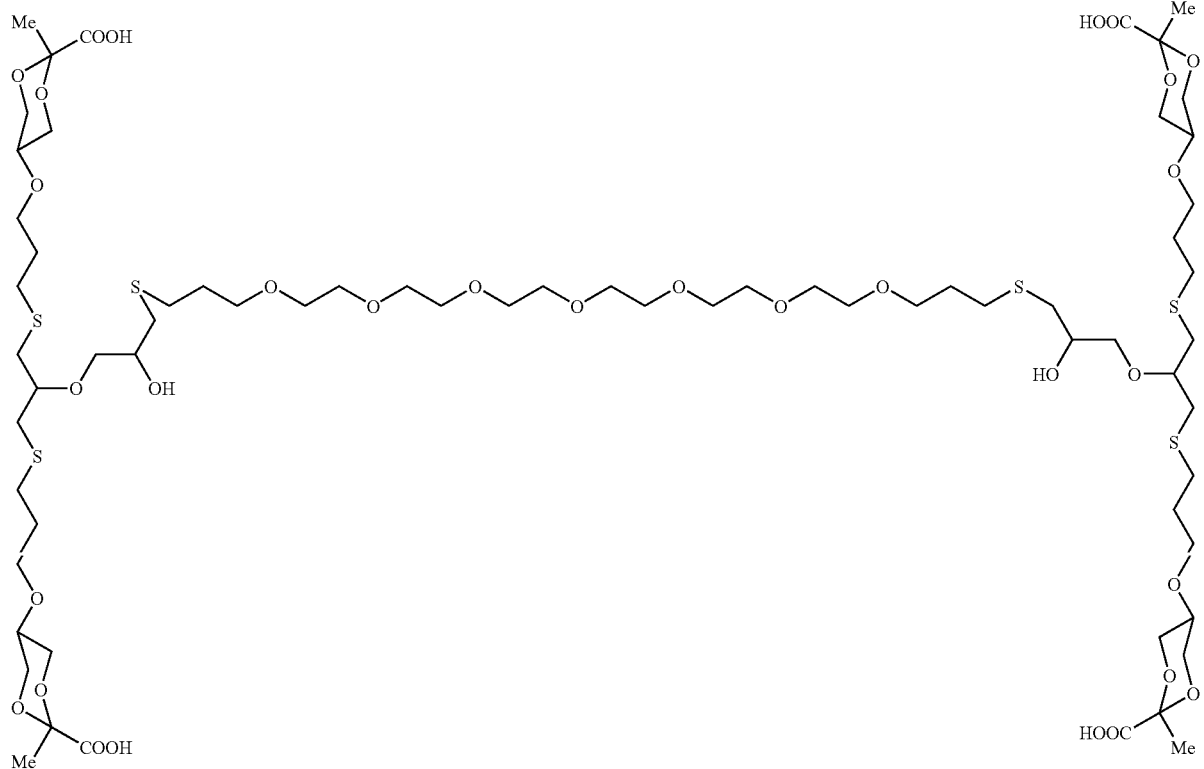

To a solution of Protected Tetramer 26 (180 mg, 0.105 mmol) in ethanol (2 ml) 1N NaOH (2.1 ml) was added and the mixture was stirred at 80° C. for 3 days. The mixture was neutralized by DOWEX (H+-form) to pH ~3 filtered and lyophilized to give the title compound Ic' (152 mg, 97%). $^1$H-NMR (D$_2$O): δ 4.12-4.08 (m, 8H, H-4e, H-6e), 3.97-3.92 (m, 2H, CH), 3.78-3.74 (m, 2H, CH), 3.71-3.63 (m, 46H, H-5, OCH$_2$), 3.53-3.48 (m, 8H, H-4a, H-6a), 2.88-2.79 (m, 10H, mmol). After 1 h the reaction was quenched with MeOH, diluted with brine and extracted with ethyl acetate. The organic layer was collected, concentrated and the residue was chromatographed on silica gel in hexane:acetone 7:3-1:1 to give a thin syrup 27 (3.35 g, 29%). $^1$H-NMR (CDCl$_3$): δ 5.95-5.88 (m, 1H, CH), 5.30-5.25 (m, 1H, CH$_2$), 5.19-5.16 (m, 1H, CH$_2$), 4.03-4.01 (m, 2H, CH$_2$), 3.74-3.59 (m, 24H, CH$_2$O). Electrospray ionization MS m/z: 345.2 (M+Na).

Example 55

21-Methanesulfonyloxy-4,7,10,13,16,19-hexa-oxa-undecosen (28)

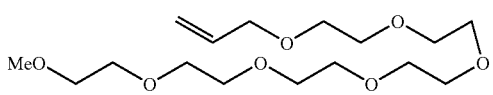

To a solution of 3,6,9,12,15,18-hexa-oxa-undecosan-20-eneol 27 (3.288 g, 10.2 mmol) in DCM (20 ml) triethylamine (2.2 ml) was added followed by methanesulfonyl chloride (1.2 ml, 15.3 mmol) at 0° C. After 1 h the mixture was diluted with DCM, washed with brine and concentrated. The residue was chromatographed on silica gel in hexane-acetone (2:1-1:1) to give a thin syrup 28 (3.33 g, 82%). $^1$H-NMR (CDCl$_3$): d 5.98-5.84 (m, 1H, CH), 5.30-5.15 (m, 2H, CH$_2$), 4.39-4.35 (m, 2H, CH$_2$), 4.07-4.00 (m, 2H, CH$_2$), 3.78-3.74 (m, 2H, CH$_2$), 3.66-3.59 (m, 20H, CH$_2$O), 3.08 (s, 3H, CH$_3$). Electrospray ionization MS m/z: 401.1 (M+H).

Example 56

1,11-Di-[((Z)-2-dimethylaminocarbonyl-6-(3,6,9,12,15,18-hexa-oxa-undecos-10-enoxy)-2-methyl-[1,3]dioxane)-5-yloxy]-4,8-di-thia-undecane

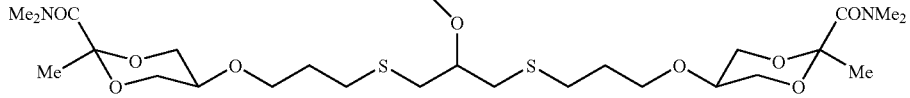

To a solution of 1,11-di-[((Z)-2-dimethylaminocarbonyl-2-methyl-[1,3]dioxane)-5-yloxy]-6-hydroxy-4,8-di-thia-undecane 24 (200 mg, 0.378 mmol) and 21-Methanesulfonyloxy-4,7,10,13,16,19-hexa-oxa-undecosen 28 (268 mg, 0.669 mmol) in dry DMF (4 ml) NaH (60%, 60 mg, 1.5 mmol) was added. After 3 h the mixture was diluted with brine, extracted with ethyl acetate and concentrated. Chromatography of the residue on silica gel in hexane-acetone (2:1-1:2) gave the title compound 29 (200 mg, 60%). $^1$H-NMR (CDCl$_3$): δ 5.94-5.88 (m, 1H, CH), 5.30-5.16 (m, 2H, CH$_2$), 4.08-4.01 (m, 6H, CH$_2$, H-4e, H-6e), 3.70-3.50 (m, 41H, H-5, H-4a, H-6a, C$\underline{H}$OH, OCH$_2$), 3.23 (s, 6H, CH$_3$), 3.01 (s, 6H, CH$_3$), 2.77-2.69 (m, 4H, CH$_2$S), 2.58 (t, 4H, J 7.0 Hz, CH$_2$S), 1.79 (p, 4H, J 7.0 Hz, SCH$_2$C$\underline{H}_2$), 1.52 (s, 6H, CH$_3$). Electrospray ionization MS m/z 909.3 (M+Na).

Example 57

1,11-di-[((Z)-2-dimethylaminocarbonyl-6-(11-acetylthio-3,6,9,12,15,18-hexa-oxa-undecosyloxy)-2-methyl-[1,3]dioxane)-5-yloxy]-4,8-di-thia-undecane (30)

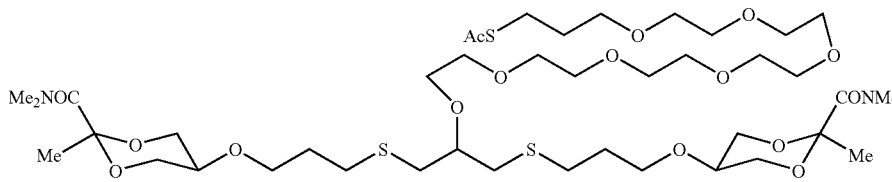

A solution of 1,11-di-[((Z)-2-dimethylaminocarbonyl-6-(3,6,9,12,15,18-hexa-oxa-undecos-10-enoxy)-2-methyl-[1,3]dioxane)-5-yloxy]-4,8-di-thia-undecane 29 (1.393 g, 1.57 mmol) and thioacetic acid (448 ml, 6.28 mmol) and a radical initiator ACCN (90 mg) in dioxane (15 ml) was stirred at 75° C. for 2 h. The mixture was concentrated and the residue was chromatographed on silica gel in hexane-acetone (2:1-1:2) to give the title compound 30 (1.171 g, 77.6%). $^1$H-NMR (CDCl$_3$): δ 4.08-4.05 (m, 4H, H-4e, H-6e), 3.70-3.50 (m, 45H, H-5, H-4a, H-6a, CHOH, OCH$_2$), 3.23 (s, 6H, CH$_3$), 3.02 (s, 6H, CH$_3$), 2.95 (t, 2H, J 7.2 Hz, CH$_2$S), 2.77-2.69 (m, 4H, CH$_2$S), 2.58 (t, 4H, J 7.1 Hz, CH$_2$S), 2.32 (s, 3H, SAc), 1.85 (p, 2H, J 6.2 Hz, SCH$_2$CH$_2$), 1.79 (p, 4H, J 6.5 Hz, SCH$_2$CH$_2$), 1.52 (s, 6H, CH$_3$). Electrospray ionization MS m/z: 985.4 (M+Na).

Example 58

1,2,3,4,5-Penta-O-glycidyl-xylitol (31)

A solution of penta-O-allyl-xylitol (722 mg, 2.048 mmol) and mCPBA (1.95 g) in chloroform (10 ml) was refluxed for 5 h. The mixture was diluted with DCM, the precipitate was filtered off, the solution was washed with aq. NaHCO$_3$ and concentrated. Chromatography of the residue on silica gel in hexane-acetone. (3:1-1:1) gave the title product 31 (757 mg, 86%). $^1$H-NMR (CDCl$_3$): δ 4.02-3.95 (m, 2H, OCH$_2$), 3.88-3.54 (m, 12H, OCH$_2$, xylitol), 3.46-3.37 (m, 3H, OCH$_2$, xylitol), 3.20-3.14 (m, 5H, CH), 2.80-2.78 (m, 5H, CH$_2$), 2.64-2.60 (m, 3H, CH$_2$), 2.58-2.56 (m, 2H, CH$_2$). Electrospray ionization MS m/z: 455.2 (M+Na).

Example 59

Protected Decamer (32)

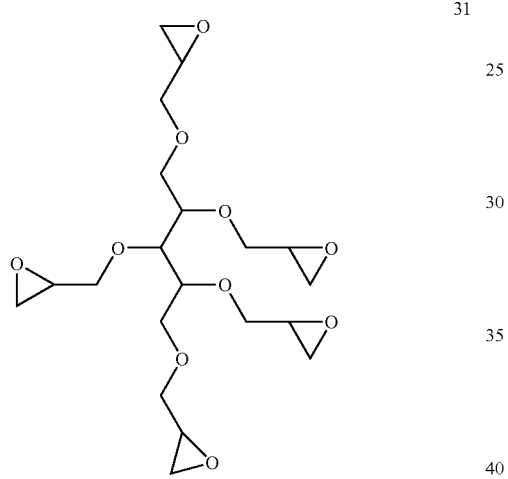

31

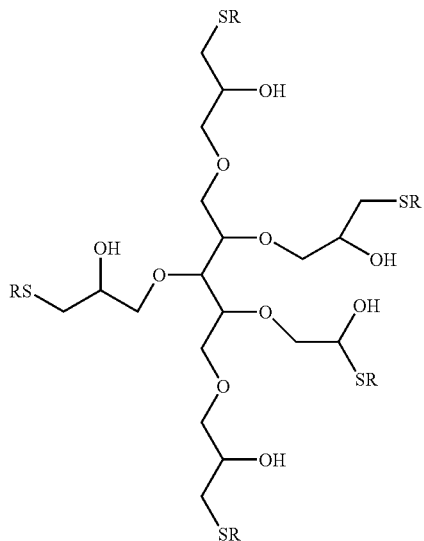

32

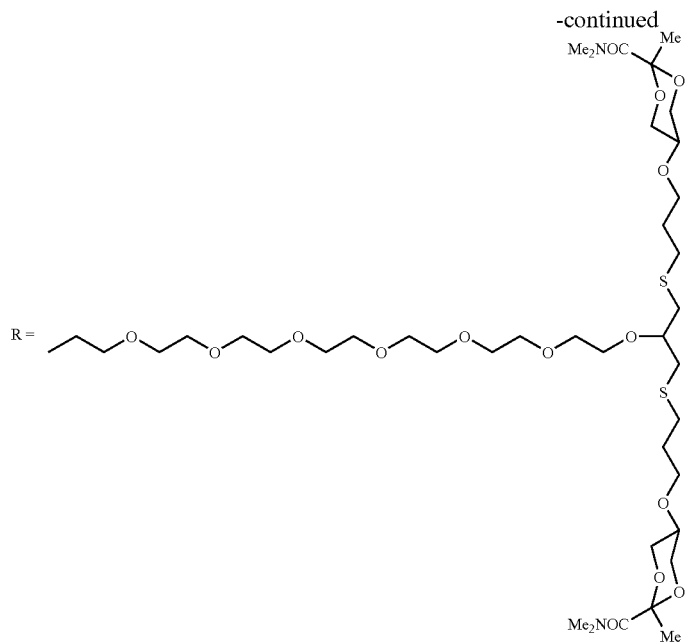

To a solution of 1,2,3,4,5-penta-O-glycidyl-xylitol 31 (44.7 mg, 0.103 mmol) and 1,11-di-[((Z)-2-dimethylaminocarbonyl-6-(11-acetylthio-3,6,9,12,15,18-hexa-oxa-undecosyloxy)-2-methyl-[1,3]dioxane)-5-yloxy]-4,8-di-thia-undecane (498 mg, 0.517 mmol) in dry MeOH (5.5 ml) $K_2CO_3$ (72 mg, 0.517 mmol) was added. After 1 h more mercaptoacetate (123 mg, 0.103 mmol) was added. After 2 h the mixture was filtered and concentrated. Chromatography of the residue on silica gel in DCM-MeOH (50:1-10:1) gave the product 32 (339 mg, 65%). $^1$H-NMR (CDCl$_3$): δ 4.08-4.05 (m, 20H, H-4e, H-6e), 3.90-3.86 (m, 5H, C$\underline{H}$OH), 3.70-3.50 (m, 207H, H-5, H-4a, H-6a, C$\underline{H}$OH, OCH$_2$), 3.23 (s, 30H, CH$_3$), 3.02 (s, 30H, CH$_3$), 2.77-2.58 (m, 60H, CH$_2$S), 1.88-1.77 (m, 30H, CH$_2$), 1.52 (s, 30H, CH$_3$). MALDI MS m/z 5062 (M+Na).

Example 60

Decamer 1 (Id')

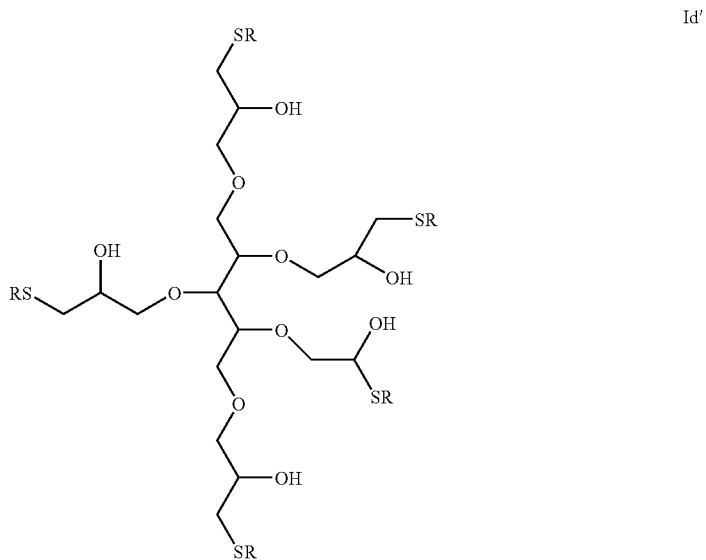

-continued

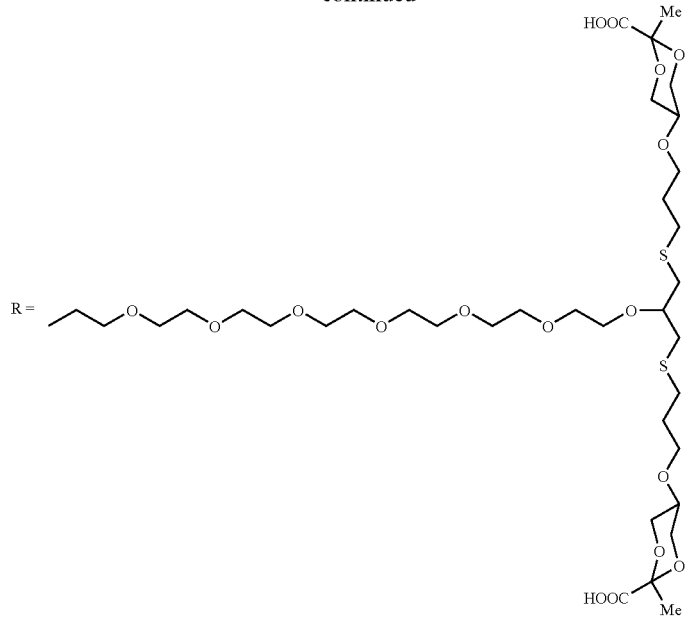

Hydrolysis of Protected Decamer 1 32 was effected by a treatment of previous compound (195 mg, 0.0387 mmol) in EtOH-water (9 ml) with 1N NaOH (2.5 ml~6.5 eq) for 2 days at 80° C. The excess NaOH was neutralized with $CO_2$. Lyophilization of the mixture gave the title compound Id' (149 mg). $^1$H-NMR ($D_2O$): δ 4.12-4.10 (m, 20H, H-4e, H-6e), 4.00-3.92 (m, 5H, C$\underline{H}$OH), 3.84-3.62 (m, 182H, H-5, C$\underline{H}$OH, OCH$_2$), 3.52-3.48 (m, 20H, H-4a, H-6a), 2.88-2.64 (m, 60H, CH$_2$S), 1.93-1.82 (m, 30H, CH$_2$), 1.42 (s, 30H, CH$_3$). MALDI MS m/z: 4766 (M+H).

Example 61

Bis-1,3-[((Z)-2-methoxycarbonyl-2-methyl-[1,3] dioxane)-5-yloxycarbonyl]-propan-2ol (Ie')

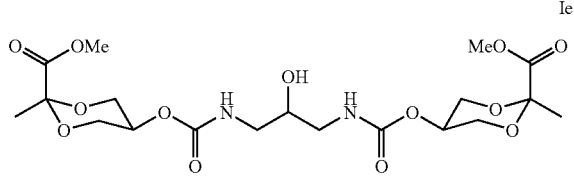

(Z)-2-Methoxycarbonyl-2-methyl-5-(p-nitrophenoxycarbonyloxy)-1,3-dioxane (4.3 g; 12.6 mmol) was dissolved in DCM (15 ml) and 1,3-diamino-2-hydroxypropane (0.45 g; 5 mmol) was added to the stirred solution followed by triethylamine (2.55 g; 25.2 mmol). The mixture was stirred for 1 h at room temperature, then filtered, concentrated and co-evaporated with toluene. The residue was chromatographed on silica gel with hexane-acetone (4:1-1:2) to give title compound Ie' as a white foam (1.86 g; 75%). $^1$H-NMR (CDCl$_3$): δ 5.25-5.20 (m, 2H, NH), 4.78 (dddd, 2H, $J_{4e,5}$=$J_{5,6e}$=5.2 Hz, $J_{4a,5}$=$J_{5,6a}$=9.3 Hz, H-5), 4.11 (dd, 4H, $J_{4a,4e}$=$J_{6a,6e}$=11.8 Hz, H-4e, H-6e), 3.82 (s, 6H, OCH$_3$), 3.75 (ddd, 1H, J 5.2 Hz, CH), 3.58 (t, 4H, H-4a, H-6a), 3.25-3.15 (m, 4H, NCH$_2$), 1.51 (s, 6H, CH$_3$). Electrospray ionization MS m/z: 517 (M+Na$^+$).

Example 62

Bis-1,3-[((Z)-2-methoxycarbonyl-2-methyl-[1,3] dioxane)-5-yloxycarbonyl]-2-(p-nitrophenoxycarbonyloxypropane (33)

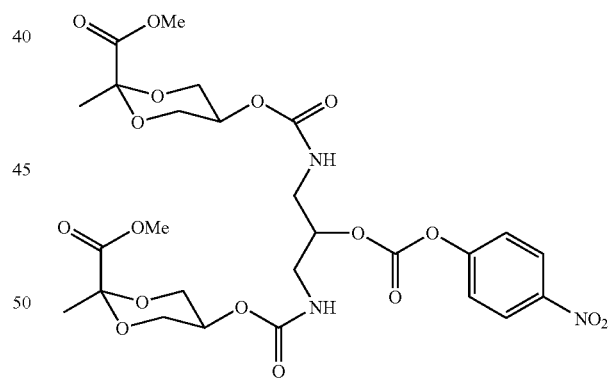

Bis-1,3-[((Z)-2-methoxycarbonyl-2-methyl-[1,3]dioxane)-5-yloxycarbonyl]-propan-2-ol (1.8 g, 3.63 mmol) and p-nitrophenyl chloroformate (0.88 g, 1.2 eq.) were dissolved in dry DCM (20 mL) and Py (0.3 mL) was added. The mixture was stirred for 0.5 h then concentrated. Chromatography of the residue on silica gel with hexane-acetone (70:30-60:40) gave 33 (2.26 g, 94%). $^1$H-NMR (CDCl$_3$): δ 8.28 and 7.39 (2 m, 4H, arom.), 5.28 (t, 2H, J 6.5 Hz, NH), 4.81 (tt, 2H, $J_{5,4e}$=$J_{5,6e}$=5.3 Hz, $J_{5,4a}$=$J_{5,6a}$=9.2 Hz, H-5), 4.75 (m, 1H, CH), 4.12 (dd, 4H, $J_{4a,4e}$=$J_{6a,6e}$=11.8 Hz, H-4e, H-6e), 3.82 (s, 6H, OCH$_3$), 3.75 (ddd, 1H, J 5.2 Hz, CH), 3.60 (dd, 4H, H-4a, H-6a), 3.53 (dt, 2 H, $^2$J 14.6 Hz, CH$_2$N), 3.39 (dt, 2H, $^2$J 14.9 Hz, CH$_2$N), 1.51 (s, 6H, CH$_3$).

Example 63

Di-1,22-(tert-butyloxycarbamoyl)-7,10,13,16-tetra-oxa-3,20-di-thia-docosane (34)

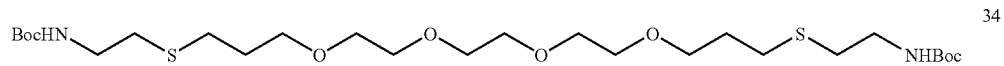

A mixture of tri(ethylene glycol) diallyl ether (5.4 g, 23.45 mmol) and 2-amino-ethanethiol hydrochloride (10 g, 92.5 mmol) in DCM (20 ml) and MeOH (15 ml) solution was stirred and irradiated with UV light for 5 hrs. Then it was treated with di-t-butyl dicarbonate (24.25 g; 111 mmol) and triethylamine (11.3 g; 111 mmol). After stirring for 0.5 h the mixture was concentrated and the residue was dissolved in DCM. The solid was filtered off, the filtrate was washed with brine, concentrated and chromatographed on silica gel with hexane-ethyl acetate (3:1-1:2) to provide title compound 34 as a colorless syrup (11.6 g; 85%). $^1$H-NMR (CDCl$_3$): δ 4.92 (broad s, 2H, NH), 3.63 (s, 4H, OCH$_2$), 3.61-3.59 (m, 4H, OCH$_2$), 3.56-3.54 (m, 4H, OCH$_2$), 3.51 (t, 4H, J 6.2 Hz, OCH$_2$), 3.27 (t, 4H, J 6.4 Hz, NCH$_2$), 2.60 (t, 4H, J 6.5 Hz, SCH$_2$), 2.57 (t, 4H, J=7.2 Hz, SCH$_2$), 1.82 (ddd, 4H, J 6.2 Hz, J 13.3 Hz, CH$_2$), 1.40 (s, 18H, tert-Bu). Electrospray ionization MS m/z: 607 (M+Na).

Example 64

1-{Bis-1,3-[((Z)-2-methoxycarbonyl-2-methyl-[1,3] dioxane)-5-yloxycarbonyl]-propanoxycarbamoyl}-22-(tert-butyloxycarbamoyl)-7,10,13,16-tetraoxa-3,20-di-thia-docosane (35)

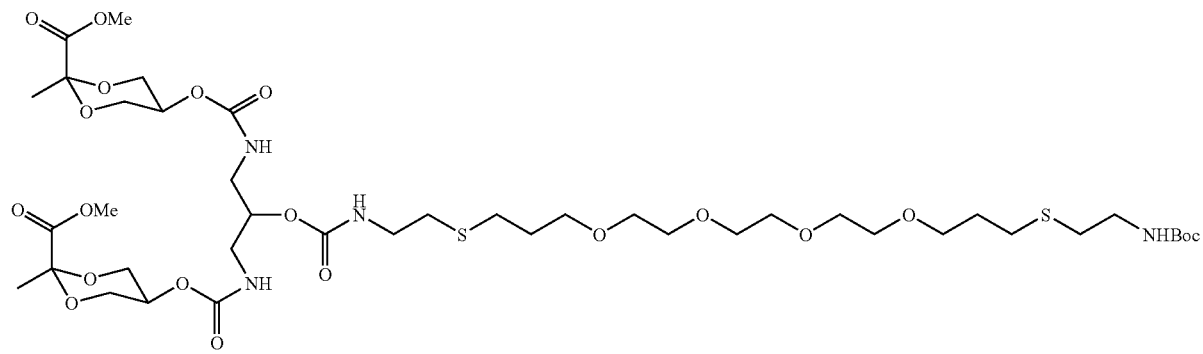

Di-1,22-(tert-butyloxycarbamoyl)-7,10,13,16-tetra-oxa-3,20-di-thia-docosane (4.43 g, 5 eq.) was dissolved in TFA (5 ml), after 30 min the solution was concentrated, co-evaporated with toluene, neutralized with Et$_3$N and dried. To the residue Et$_3$N (2 ml) and a solution of bis-1,3-[((Z)-2-methoxycarbonyl-2-methyl-[1,3]dioxane)-5-yloxycarbonyl]-2-(p-nitrophenoxycarbonyloxypropane (1 g, 1.51 mmol) in DCM (5 ml) were added. The reaction mixture was stirred 30 min then (t-BuO)$_2$CO (12 eq) was added, the mixture was concentrated and chromatophraphed on silica gel with hexane-acetone (80:20-1:1) to give the title compound 35 (1.36 g, 89%). $^1$H-NMR (CDCl$_3$): δ 5.36-5.26 (m, 3H, NH), 4.97-4.90 (m, 1H, NH), 4.82-4.76 (m, 2H, H-5), 4.72-4.66 (m, 1H, CHO), 4.14-4.10 (m, 4H, H-4e, H-6e), 3.82 (s, 6H, OCH$_3$), 3.64-3.52 (m, 20H, H-4a, H-6a, CH$_2$O), 3.36-3.25 (m, 8H, CH$_2$N), 2.65-2.57 (m, 8H, CH$_2$S), 1.85-1.80 (m, 4H, CH$_2$), 1.51 (s, 6H, CH$_3$), 1.42 (s, 9H, t-Bu). Electrospray ionization MS m/z: 1027 (M+Na).

Example 65

1-{Bis-1,3-[((Z)-2-methoxycarbonyl-2-methyl-[1,3]dioxane)-5-yloxycarbonyl]-propanoxycarbamoyl}-22-(4-ethoxy-cyclobutene-2,3-dionylamino)-7,10,13,16-tetra-oxa-3,20-di-thia-docosane (36)

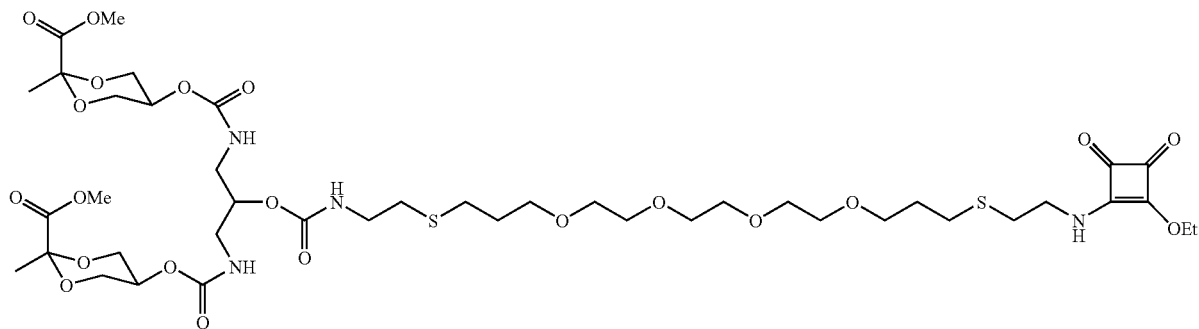

1-{Bis-1,3-[((Z)-2-methoxycarbonyl-2-methyl-1,3-dioxane)-5-yloxycarbonyl]-propanoxycarbamoyl}-22-(tert-butyloxycarbamoyl)-7,10,13,16-tetra-oxa-3,20-di-thia-docosane (917 mg 0.912 mmol) was dissolved in TFA (3 mL) after 30 min the solution was concentrated, co-evaporated with toluene, dissolved in 10 mL MeOH and pH was adjusted to 8 with concentrated solution of NaHCO$_3$. 2,3-Di-ethoxy-3-cyclobutene-1,2-dione (200 mg, 1.5 eq) was added. The mixture was concentrated to the volume of 0.5 mL, suspended in DCM and layers separated. Organic fraction was concentrated and chromatographed on silica gel with hexane-acetone (50:50-40:60) to give the title compound 36 (802 mg, 85%). $^1$H-NMR (CDCl$_3$): δ 5.60-5.30 (m, 3H, NH), 4.82-4.68 (m, 5H, H-5, C$\underline{H}_2$CH$_3$, CHO), 4.14-4.08 (m, 4H, H-4e, H-6e), 3.82 (s, 6H, OCH$_3$), 3.64-3.52 (m, 22H, H-4a, H-6a, CH$_2$O, CH$_2$N), 3.36-3.24 (m, 6H, CH$_2$N), 2.76-2.56 (m, 8H, CH$_2$S), 1.85-1.80 (m, 4H, CH$_2$), 1.51 (s, 6H, CH$_3$), 1.44 (t, 3H, CH$_3$). Electrospray ionization MS m/z: 1051 (M+Na).

Example 66

Decamer 2 (If')

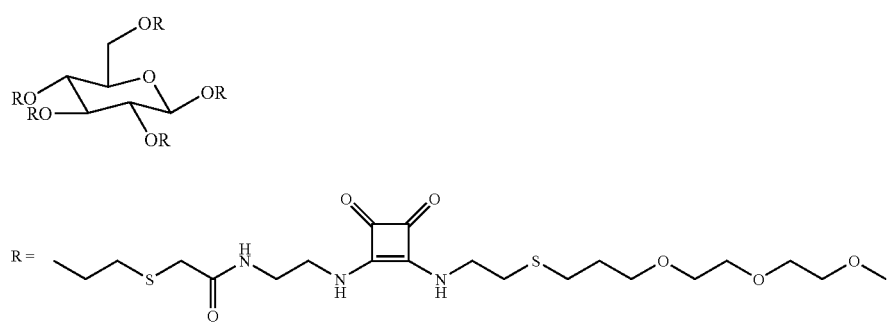

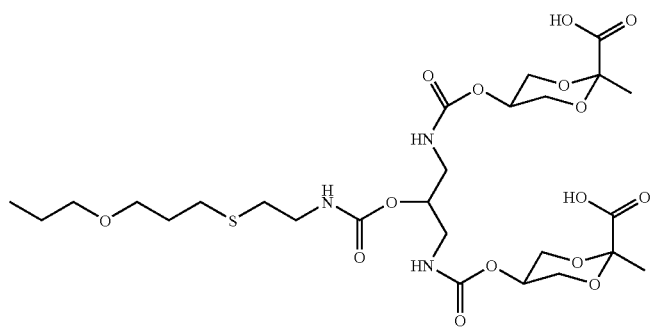

1,2,3,4,6-Penta-O-(7-aza-9-tert-butoxycarbonylamino-4-thia-non-6-onyl)-b-D-glucopyranoside (43 mg, 27.7 mmol) was dissolved in TFA (1 mL). After 30 min the mixture was evaporated, co-evaporated with EtOH. The residue was dissolved in MeOH (2 mL) and dry $KHCO_3$ was added. The supernatant was added to a solution of 1-{Bis-1,3-[((Z)-2-methoxycarbonyl-2-methyl-[1,3]dioxane)-5-yloxycarbonyl]-propanoxycarbamoyl}-22-(4-ethoxy-cyclobutene-2,3-dionylamino)-7,10,13,16-tetra-oxa-3,20-di-thia-docosane (200 mg, 0.19 mmol) in MeOH (3 mL). Fresh $KHCO_3$ was added and the suspension was stirred 3 days. The solution was chromatographed on silica gel with DCM-MeOH (10:1) to give the pentamer (65 mg, 40%). To a solution of the residue in MeOH (3 ml) 1 N NaOH (120 ml) was added and the mixture was stirred overnight at room temperature. The excess NaOH was neutralized with $CO_2$, the solution was concentrated and lyophilized to give white powder If' (130 mg). $^1$H-NMR ($D_2O$): d 4.14-4.08 (m, 20H, H-4e, H-6e), 3.85-3.52 (m, 147H, H-4a, H-6a, H-5, $CH_2O$), 3.50-3.45 (m, 10H, $CH_2N$), 3.35-3.22 (m, 50H, $CH_2N$), 3.10-2.90 (m, 10H, $CH_2S$), 2.83-2.80 (m, 10H, $CH_2S$), 2.70-2.57 (m, 40H, $CH_2S$), 2.10-2.00 (m, 10H, $CH_2$), 1.90-1.80 (m, 30H, $CH_2$), 1.49 (s, 30H, $CH_3$).

Example 67

Inhibition of Binding of SAP to an Immobilized D-Proline Derivative

A 96 well polystyrene ELISA plate was coated with a solution of N-10-undecenoyl-D-proline (1 µg/ml, 100 µL) in 0.05 M carbonate buffer pH 9.8. After overnight incubation at 4° C. the plates were washed (5×300 µL) with 10 mM Tris Buffer Saline pH 8 supplemented with 2.5 mM $CaCl_2$ (TBS-Ca). SAP stock solution (2 µg/ml) was prepared by dilution of 1 mg/ml solution (stabilized by 10 mmol EDTA) with TBS-Ca. An inhibitor solution in TBS-Ca (50 µL) was mixed with SAP stock solution (50 µL) and incubated for 2 h at room temperature. The wells were washed with TBS-Ca (5×300 µL). Mouse monoclonal anti-human SAP IgG (1:2000 dilution) in TBS-Ca (100 µL) was added to the wells and incubated for 1 h at room temperature. The wells were washed with TBS-Ca (5×300 µL). Goat anti-mouse IgG labeled with hoarse radish peroxidase (1:2000 dilution) in TBS-Ca (100 µL) was added to the wells and incubated for 1 h at room temperature. The wells were washed with TBS-Ca (5×300 µL). A solution of peroxidase substrate TMB (100 µL) was added and the reaction was quenched with $H_3PO_4$ after 2-5 min. Absorption was measured on ELISA reader.

Activities ($IC_{50}$) of the tested compounds were in the range of 0.001-20 mg/ml.

Example 68

Crystal Structures of SAP Complexes

Crystals of SAP in the presence of compounds Ib and II were obtained by the hanging drop vapour diffusion method. Diffraction data were measured from single crystals flash frozen under a nitrogen cryo stream (~110 K) using a MAR image plate and X-rays produced with a rotating copper anode (Rigaku RU300H). Higher resolution data were also measured on single crystals using an ADSC Quantum-315 CCD detector at the Advanced Light Source on beamline 8.3.1 (λ=1.115 Å). The data were processed, scaled and merged using DENZO and programs from CCP4. Crystals grown in the presence of compound Ib belong to space group P1 and crystals grown in the presence of compound II belong to space group $P2_1$ for all molecular replacement calculations. The structures of SAP complexed with compounds Ib and II were determined using molecular replacement using the protein chains from the SAP pentamer of the 2'-dAMP complex (PDB code 1LGN) as the search model. The programs AmoRe and CNS were used for molecular replacement calculations, and the structure was refined using the program Refmac.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A compound of Formula I

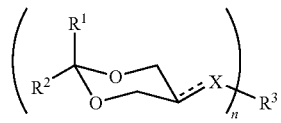

wherein
R$^1$ is selected from the group consisting of $CO_2H$ and tetrazole;
R$^2$ is $C_{1-6}$ alkyl;
----- is a single or a double bond such that when ----- is a single bond, X is selected from the group consisting of O, S, NH, $CH_2$, OC(O) and O(CO)NH, and when ----- is a double bond, X is selected from the group consisting of O, S, N and CH;
R$^3$ is selected from the group consisting of a small oligosaccharide or saccharide, a small peptide, a small oligocarbamate, a small molecule which binds to a serum amyloid P component (SAP) surface adjacent to a $Ca^{2+}$-dependent binding site, $(LA)_m$, $(LA)_m$MFC and when ----- is a double bond and X is O or S, R$^3$ is non-existent;
n is an integer between, and including, 1 and 20;
m is an integer between and including, 1 and 20;
LA is a linker arm selected from the group consisting of arylene, a peptide chain, oligocarbamate, $C_{2-60}$ straight, branched or cyclic alkylene and $C_{2-60}$ straight, branched or cyclic alkenylene, wherein in both alkylene and alkenylene, one or more of the carbons may optionally be replaced with an O, S, N and/or NR$^6$ and optionally interrupted by arylene, and the linker arms can optionally be functionalized at one or more positions with a group selected from aryl, heteroaryl, heterocyclo, $C_{3-8}$cycloalkyl, OH, O-aryl, O-heteroaryl O-heterocyclo, O—$C_{3-8}$cycloalkyl and O—$C_{1-6}$ alkyleneheterocyclo, wherein the aryl, heteroaryl, cycloalkyl and heterocyclo may each be independently optionally substituted;
R$^6$ is selected from the group consisting of H and $C_{1-6}$ alkyl;
MFC is a multifunctional core group; and
pharmaceutically acceptable salts, hydrates, solvates and prodrugs thereof.

2. The compound according to claim 1, wherein the compound of Formula I has one of the following general structures:

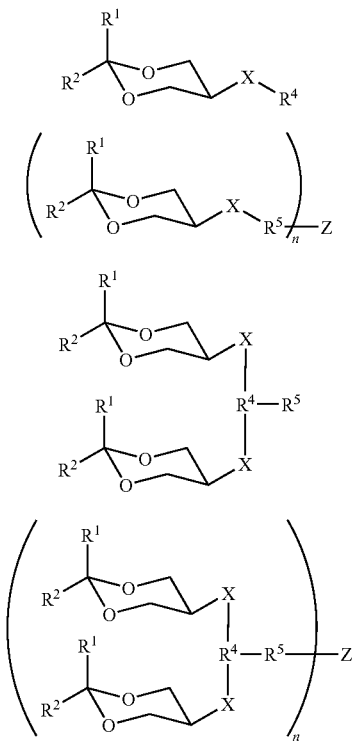

wherein:
R$^1$ is selected from the group consisting of CO$_2$H and tetrazole;
R$^2$ is C$_{1-6}$alkyl;
each X is independently selected from the group consisting of O, S, NH, CH$_2$, OC(O) and O(CO)NH;
each n is independently an integer between, and including 1-20;
each R$^4$ is independently selected from the group consisting of a small oligosaccharide or saccharide, a small peptide, a small oligocarbamate and a small molecule which binds to a serum amyloid p component (SAP) surface adjacent to a Ca$^{2+}$-dependent binding site;
each R$^5$ is a linker group independently selected from the group consisting of arylene, a peptide chain, oligocarbamate, C$_{2-60}$ straight, branched or cyclic alkylene, and C$_{2-60}$ straight, branched or cyclic alkenylene, wherein in both alkylene and alkenylene, one or more of the carbons may optionally be replaced with an O, S, N and/or NR$^6$ and optionally interrupted by arylene, and the linker arms can optionally be functionalized at one or more positions with a group selected from aryl, heteroaryl, heterocyclo, C cycloalkyl, OH, O-aryl, O-heteroaryl, O-heterocyclo, O—C$_{3-8}$cycloalkyl and O—C$_{1-6}$alkyleneheterocyclo, wherein the aryl, heteroaryl, cycloalkyl and heterocyclo groups may each be independently optionally substituted;
R$^6$ is selected from the group consisting of H and C$_{1-6}$alkyl;
each Z is, independently, a multifunctional core (MFC) group, and
pharmaceutically acceptable salts, hydrates, solvates and prodrugs thereof.

3. The compound according to claim 1, wherein R$^1$ is CO$_2$H, CO$_2$Me or CO$_2$Et.

4. The compound according to claim 3, wherein R$^1$ is CO$_2$H.

5. The compound according to claim 1, wherein R$^2$ is C$_{1-4}$alkyl.

6. The compound according to claim 5, wherein R$^2$ is methyl or ethyl.

7. The compound according to claim 6, wherein R$^2$ is methyl.

8. The compound according to claim 1, wherein X is selected from the group consisting of O, S, OC(O) and O(CO)NH.

9. The compound according to claim 2, wherein the compound is selected from a compound of Formula I-B, I-C and I-D.

10. The compound according to claim 1, wherein the linker arms or linker groups R$^3$, are selected from the group consisting of phenylene, an amino acid, such as alanine, C$_{2-30}$ straight, branched or cyclic alkylene, and C$_{2-30}$ straight, branched or cyclic alkenylene, wherein in both alkylene and alkenylene, one or more of the carbons may optionally be replaced with an O and/or S and optionally interrupted by arylene, and the linker arms or groups can optionally be functionalized at one or more positions with a group selected from phenyl, OH, O-phenyl and O-saccharide, wherein the phenyl group is optionally substituted.

11. The compound according to claim 10, wherein the linker arms or linker groups R$^3$ are selected from 1,4-phenylene; 1,3-phenylene; 1,2-phenylene; C$_{2-20}$ alkylene optionally substituted with OH and a saccharide, and one or more of the carbons may optionally be replaced with an O and/or S;

—(CH$_2$)$_p$—Ph—(CH$_2$)$_p$ wherein p is an integer between, and including, 1-6, specifically, 1-4, more specifically 1;

—(CH$_2$)$_p$—CH=CH—(CH$_2$)$_p$ wherein p is an integer between, and including, 1-6, specifically, 1-4, more specifically 1;

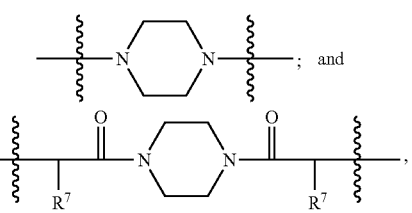

wherein R$^7$ is the sidechain of an amino acid, specifically CH$_3$, CH$_2$Ph, CH(CH$_3$)$_2$, more specifically CH$_3$.

12. The compound according to claim 11, wherein the saccharide is β-D-glucopyranosyl.

13. The compound according to claim 1, wherein the multifunctional core group is a biocompatible multifunctional molecule comprising between three and 20 reactive sites which couple with a linker arm.

14. The compound according to claim 13, wherein the multifunctional core group is selected from monosaccharides, disaccharides, trisaccharides, short chain polylysines, polysubstituted aromatics, cycloalkanes, polyacrylamides, cyclodextrins, phthalocyanins, oligosaccharides, inositols, and alditols.

15. The compound according to claim 13, wherein the multifunctional core group is an organic polyol.

16. A compound according to claim 1, selected from the group consisting of:
- Bis-1,2-{[(Z)-2-ethoxycarbonyl-2-methyl-[1,3]dioxane]-5-yloxycarbamoy-1}-ethane (Ia)
- Bis-1,2-{[(Z)-2-carboxy-2-methyl-[1,3]dioxane]-5-yloxycarbam-oyl}-ethane (Ib)
- Bis-1,3-[((Z)-2-methoxycarbonyl-2-methyl-[1,3]dioxane)-5-yloxycarbam-oyl]-propane (Ic)
- Bis-1,3-[((Z)-2-carboxy-2-methyl-[1,3]dioxane)-5-yloxycarbamoyl]-propane (Id)
- Bis-1,4-{[(Z)-2-ethoxycarbonyl-2-methyl-[1,3]dioxane]-5-yloxycarbamo-yl}-butane (Ie)
- Bis-1,4-{[(Z)-2-carboxy-2-methyl-[1,3]-dioxane]-5-yloxycarbamoyl}-butane (If)
- Bis-1,5-{[(Z)-ethoxycarbonyl-2-methyl-[1,3]dioxane]-5-yloxycarbamoyl}-pentane (Ig)
- Bis-1,5-{[(Z)-2-carboxy-2-methyl-[1,3]dioxane]-5-yloxycarbamoyl}-pentane (Ih)
- Bis-1,6-{[(Z)-2-methoxycarbonyl-2-methyl-[1,3]dioxane]-5-yloxycarbam-oyl}-hexane (Ii)
- Bis-1,6-{[(Z)-2-carboxy-2-methyl-[1,3]dioxane]-5-yloxycarbamoyl}-hexane (Ij)
- Bis-N,N-{[(Z)-2-ethoxycarbonyl-2-methyl-[1,3]dioxane]-5-yloxycarbony-l}-piperazine (Ik)
- Bis-N,N-{[(Z)-2-carboxy-2-methyl-[1,3]dioxane]-5-yloxycarbonyl}-piperazine (Il)
- Bis-N,N-{[(Z)-2-ethoxycarbonyl-2-methyl-[1,3]dioxane]-5-yloxycarbonyl-L-alanylo}-piperazine (Im)
- Bis-N,N-{[(Z)-2-carboxy-2-methyl-[1,3]dioxane)-5-yloxycarbonyl-L-alanylo]-piperazine (In)
- Bis-1,3-[((Z)-2-ethoxycarbonyl-2-methyl-[1,3]dioxane)-5-yloxycarbonyl]-propan-2-ol (Io)
- Bis-1,3-{[(Z)-2-ethoxycarbonyl-2-methyl-[1,3]dioxane)-5-yloxycarbamoyl]-2-O-(2,3,4,6-tetra-O-acetylo-b-D-lucopyranozylo)-propan-2-ol (Ip)
- Bis-1,3-{[(Z)-2-carboxy-2-methyl-1,3-dioxane)-5-yloxycarbamoyl]-2-O-(β-D-glucopyranozylo)-propan-2-ol (Iq)
- Bis-1,4-[((Z)-2-carboxy-2-methyl-[1,3]dioxane)-5-yloxymethyl]-benzene (Ir)
- Bis-1,3-[((Z)-2-carboxy-2-methyl-[1,3]dioxane)-5-yloxymethyl]-benzene (Is)
- Bis-1,2-[((Z)-2-carboxy-2-methyl-[1,3]dioxane)-5-yloxymethyl]-benzene (It)
- Bis-1,4-[((Z)-2-carboxy-2-methyl-1,3-dioxane)-5-yloxymethyl]-but-2-ene (Iu)
- Bis-1,6-[((Z)-2-carboxy-2-methyl-[1,3]dioxane)-5-yloxy]-hexane (Iv)
- Bis-1,3-[((E)-2-carboxy-2-methyl-[1,3]dioxane)-5-ylthio]-2-hydroxy-propane (Iw)
- Bis-1,6-[((E)-2-carboxy-2-methyl-[1,3]dioxane)-5-ylthio]-hexane (Ix)
- Bis-1,4-[((E)-2-carboxy-2-methyl-[1,3]dioxane)-5-ylthio]-but-2-ene (Iy)
- Bis-1,4-[((E)-2-carboxy-2-methyl-[1,3]dioxane)-5-thiomethyl]-benzene (Iz)
- 5,9-Di-{[((Z)-2-carboxy-2-methyl-[1,3]dioxane)-5-yloxy]methyl}-2,12-di-hydroxy-1-mercapto-4,10,18,21,24,27,30,33,36-nona-oxa-7,14-di-thia-nonatriacontane (Ia')
- 1,11-Di-[((Z)-2-carboxy-2-methyl-[1,3]dioxane)-5-yloxy]-6-hydroxy-4,8-di-thia-undecane (Ib')
- 1,1,37,37-Tetra-{5-[((Z)-2-carboxy-2-methyl-[1,3]dioxane)-5-yloxy]-2-thia-pentyl}-4,34-di-hydroxy-2,10,13,16,19,22,25,28,36-nona-oxa-6,32-di-thia-heptatriacontane (Ic')
- Decamer 1 (Id')
- Bis-1,3-[((Z)-2-methoxycarbonyl-2-methyl-[1,3]dioxane)-5-yloxycarbonyl]-propan-2-ol (Ie')
- Decamer 2 (If')

and pharmaceutically acceptable salts, hydrates, solvates and prodrugs thereof.

17. A method of treating or preventing amyloidosis comprising administering an effective amount of a compound according to claim 1 to an animal in need thereof.

18. A method of treating diseases associated with amyloidosis comprising administering an effective amount of a compound according to claim 1 to an animal in need thereof.

19. A pharmaceutical composition comprising a compound according to claim 1 and a pharmaceutically acceptable carrier.

20. The compound according to claim 2, wherein $R^1$ is $CO_2H$, $CO_2Me$ or $CO_2Et$.

21. The compound according to claim 20, wherein $R^1$ is $CO_2H$.

22. The compound according to claim 2, wherein $R^2$ is $C_{1-4}$ alkyl.

23. The compound according to claim 22, wherein $R^2$ is methyl or ethyl.

24. The compound according to claim 23, wherein $R^2$ is methyl.

25. The compound according to claim 2, wherein X is selected from the group consisting of O, S, OC(O) and O(CO)NH.

26. The compound according to claim 2, wherein the linker arms or linker groups $R^5$, are selected from the group consisting of phenylene, an amino acid, such as alanine, $C_{2-30}$ straight, branched or cyclic alkylene, and $C_{2-30}$ straight, branched or cyclic alkenylene, wherein in both alkylene and alkenylene, one or more of the carbons may optionally be replaced with an O and/or S and optionally interrupted by arylene, and the linker arms or groups can optionally be functionalized at one or more positions with a group selected from phenyl, OH, O-phenyl and O-saccharide, wherein the phenyl group is optionally substituted.

27. The compound according to claim 26, wherein the linker arms or linker groups $R^5$ are selected from 1,4-phenylene; 1,3-phenylene; 1,2-phenylene; $C_{2-20}$ alkylene optionally substituted with OH and a saccharide, and one or more of the carbons may optionally be replaced with an O and/or S;

—$(CH_2)_p$-Ph-$(CH_2)_p$ wherein p is an integer between, and including, 1-6, specifically, 1-4, more specifically 1;

—$(CH_2)_p$—CH=CH—$(CH_2)_p$ wherein p is an integer between, and including, 1-6, specifically, 1-4, more specifically 1;

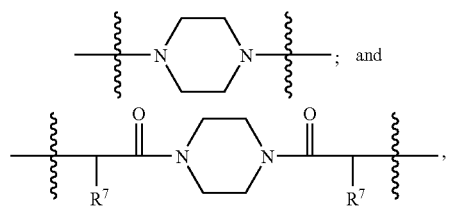

wherein $R^7$ is the sidechain of an amino acid, specifically $CH_3$, $CH_2Ph$, $CH(CH_3)_2$, more specifically $CH_3$.

28. The compound according to claim 27, wherein the saccharide is β-D-glucopyranosyl.

29. The compound according to claim 2, wherein the multifunctional core group is a biocompatible multifunctional molecule comprising between three and 20 reactive sites which couple with a linker arm.

30. The compound according to claim 29, wherein the multifunctional core group is selected from monosaccharides, disaccharides, trisaccharides, short chain polylysines, polysubstituted aromatics, cycloalkanes, polyacrylamides, cyclodextrins, phthalocyanins, oligosaccharides, inositols, and alditols.

31. The compound according to claim 29, wherein the multifunctional core group is an organic polyol.

32. A method of treating or preventing amyloidosis comprising administering an effective amount of a compound according to claim 2 to an animal in need thereof.

33. A method of treating diseases associated with amyloidosis comprising administering an effective amount of a compound according claim 2 to an animal in need thereof.

34. A pharmaceutical composition comprising a compound according to claim 2 and a pharmaceutically acceptable carrier.

* * * * *